(12) United States Patent
Hudson et al.

(10) Patent No.: US 8,592,138 B2
(45) Date of Patent: Nov. 26, 2013

(54) METHODS FOR IMPROVING SPERM FUNCTIONALITY

(75) Inventors: Keith Hudson, Auckland (NZ); Bridget Lee Dicker, Auckland (NZ); Jiwon Hong, Auckland (NZ); Shakeela Nathalia Jayasinghe, Manukau (NZ)

(73) Assignee: Androgenix Ltd., Auckland (NZ)

( * ) Notice: Subject to any disclaimer, the term of this patent is extended or adjusted under 35 U.S.C. 154(b) by 0 days.

(21) Appl. No.: 13/578,576

(22) PCT Filed: Feb. 9, 2011

(86) PCT No.: PCT/NZ2011/000019
§ 371 (c)(1),
(2), (4) Date: Sep. 12, 2012

(87) PCT Pub. No.: WO2011/099872
PCT Pub. Date: Aug. 18, 2011

(65) Prior Publication Data
US 2012/0329035 A1 Dec. 27, 2012

Related U.S. Application Data

(60) Provisional application No. 61/304,197, filed on Feb. 12, 2010, provisional application No. 61/424,511, filed on Dec. 17, 2010.

(51) Int. Cl.
*C12N 5/076* (2010.01)
(52) U.S. Cl.
USPC ............................................. 435/2; 435/375
(58) Field of Classification Search
USPC ...................................................... 435/2, 375
See application file for complete search history.

(56) References Cited

U.S. PATENT DOCUMENTS 4,722,887 A * 2/1988 Fabricant et al. ................. 435/2

FOREIGN PATENT DOCUMENTS

WO WO 2005/054808 * 6/2005 ............... A01N 1/02

OTHER PUBLICATIONS

Andrabi, Smh, "Factors Affecting the Quality of Cryopreserved Buffalo (*Bubalus bubalis*) Bull Sprematozoa," Reprod. Dom. Anim., vol. 44, pp. 552-569 (2009).
David, C.J. et al., "Maternal and Paternal Hybrid Triploids of Tetras," Journal of Fish Biology, vol. 69, pp. 1102-1119 (2006).
Hunter, Stephen K. et al., "The Gamete and Embryo Compatibility of Various Synthetic Polymers," Fertility and Sterility, vol. 50, No. 1, pp. 110-116 (Jul. 1988).
Moura, Arlindo A., et al., "Protein of the Accessory Sex Glands Associated with the Oocyte-Penetrating Capacity of Cauda Epididymal Sperm from Holstein Bulls of Documented Fertility," Molecular Reproduction and Development, vol. 74, No. 2, pp. 214-222 (2007).
Rodriguez-Martinez, H. et al., "The Physiological Roles of the Boar Ejaculate," Society of Reproduction and Fertility, Supplement vol. 66, pp. 1-21 (2009.

* cited by examiner

*Primary Examiner* — Karen Cochrane Carlson
*Assistant Examiner* — Jennifer M Tichy
(74) *Attorney, Agent, or Firm* — Janet Sleath; Speckman Law Group PLLC

(57) ABSTRACT

Methods for improving the functionality and/or fertility of sperm, for example, by enhancing motility and extending the lifespan of sperm in the female reproductive tract, by adding PEG to the surface of the sperm are provided. Such methods may be used in artificial insemination to reduce the number of sperm needed for insemination and to improve conception rates.

17 Claims, No Drawings ved in the standard AI

SEQUENCE LISTING

<160> NUMBER OF SEQ ID NOS: 5

<210> SEQ ID NO 1
<211> LENGTH: 134
<212> TYPE: PRT
<213> ORGANISM: Bos taurus

<400> SEQUENCE: 1

```
Met Ala Leu Gln Leu Gly Leu Phe Leu Ile Trp Ala Gly Val Ser Val
  1               5                  10                  15

Phe Leu Gln Leu Asp Pro Val Asn Gly Asp Gln Asp Glu Gly Val Ser
             20                  25                  30

Thr Glu Pro Thr Gln Asp Gly Pro Ala Glu Leu Pro Glu Asp Glu Glu
         35                  40                  45

Cys Val Phe Pro Phe Val Tyr Arg Asn Arg Lys His Phe Asp Cys Thr
     50                  55                  60

Val His Gly Ser Leu Phe Pro Trp Cys Ser Leu Asp Ala Asp Tyr Val
 65                  70                  75                  80

Gly Arg Trp Lys Tyr Cys Ala Gln Arg Asp Tyr Ala Lys Cys Val Phe
                 85                  90                  95

Pro Phe Ile Tyr Gly Gly Lys Lys Tyr Glu Thr Cys Thr Lys Ile Gly
            100                 105                 110

Ser Met Trp Met Ser Trp Cys Ser Leu Ser Pro Asn Tyr Asp Lys Asp
            115                 120                 125

Arg Ala Trp Lys Tyr Cys
        130
```

<210> SEQ ID NO 2
<211> LENGTH: 140
<212> TYPE: PRT
<213> ORGANISM: Bos taurus

<400> SEQUENCE: 2

```
Met Ala Leu Arg Leu Gly Leu Phe Leu Ile Trp Ala Gly Val Ser Met
  1               5                  10                  15

Phe Leu Gln Leu Asp Pro Val Asn Gly Asp Glu Gln Leu Ser Glu Asp
             20                  25                  30

Asn Val Ile Leu Pro Lys Glu Lys Lys Asp Pro Ala Ser Gly Ala Glu
             35                  40                  45

Thr Lys Asp Asn Lys Cys Val Phe Pro Phe Ile Tyr Gly Asn Lys Lys
     50                  55                  60

Tyr Phe Asp Cys Thr Leu His Gly Ser Leu Phe Leu Trp Cys Ser Leu
 65                  70                  75                  80

Asp Ala Asp Tyr Thr Gly Arg Trp Lys Tyr Cys Thr Lys Asn Asp Tyr
                 85                  90                  95

Ala Lys Cys Val Phe Pro Phe Ile Tyr Glu Gly Lys Ser Tyr Asp Thr
            100                 105                 110

Cys Ile Ile Ile Gly Ser Thr Phe Met Asn Tyr Trp Cys Ser Leu Ser
            115                 120                 125

Ser Asn Tyr Asp Glu Asp Gly Val Trp Lys Tyr Cys
        130                 135                 140
```

<210> SEQ ID NO 3
<211> LENGTH: 183
<212> TYPE: PRT
<213> ORGANISM: Bos taurus

<400> SEQUENCE: 3

```
Met Ala Pro Leu Val Gly Leu Phe Leu Ile Trp Ala Gly Ala Ser Val
  1               5                  10                  15

Phe Gln Gln Leu His Pro Val Asn Gly Gly Asp Ile Pro Asp Pro Gly
             20                  25                  30

Ser Lys Pro Thr Pro Pro Gly Met Ala Asp Glu Leu Pro Thr Glu Thr
         35                  40                  45
```

```
Tyr Asp Leu Pro Pro Glu Ile Tyr Thr Thr Thr Phe Leu Pro Arg Thr
     50                  55                  60

Ile Tyr Pro Gln Glu Glu Met Pro Tyr Asp Asp Lys Pro Phe Pro Ser
 65                  70                  75                  80

Leu Leu Ser Lys Ala Asn Asp Leu Asn Ala Val Phe Glu Gly Pro Ala
                 85                  90                  95

Cys Ala Phe Pro Phe Thr Tyr Lys Gly Lys Lys Tyr Tyr Met Cys Thr
                100                 105                 110

Arg Lys Asn Ser Val Leu Leu Trp Cys Ser Leu Asp Thr Glu Tyr Gln
                115                 120                 125

Gly Asn Trp Lys Phe Cys Thr Glu Arg Asp Pro Glu Cys Val Phe
                130                 135                 140

Pro Phe Ile Tyr Arg Lys Lys Ser Tyr Glu Ser Cys Thr Arg Val His
145                 150                 155                 160

Ser Phe Phe Trp Arg Arg Trp Cys Ser Leu Thr Ser Asn Tyr Asp Arg
                165                 170                 175

Asp Lys Ala Trp Lys Tyr Cys
                180

<210> SEQ ID NO 4
<211> LENGTH: 134
<212> TYPE: PRT
<213> ORGANISM: Bos taurus

<400> SEQUENCE: 4

Met Lys Leu Ser Ser Val Ile Pro Trp Ala Leu Leu Leu Ser Thr Ala
  1               5                  10                  15

Thr Val Asp Ser Met Asp Trp Leu Pro Arg Asn Thr Asn Cys Gly Gly
                 20                  25                  30

Ile Leu Lys Glu Glu Ser Gly Val Ile Ala Thr Tyr Tyr Gly Pro Lys
                 35                  40                  45

Thr Asn Cys Val Trp Thr Ile Gln Met Pro Pro Glu Tyr His Val Arg
     50                  55                  60

Val Ser Ile Gln Tyr Leu Gln Leu Asn Cys Asn Lys Glu Ser Leu Glu
 65                  70                  75                  80

Ile Ile Asp Gly Leu Pro Gly Ser Pro Val Leu Gly Lys Ile Cys Glu
                 85                  90                  95

Gly Ser Leu Met Asp Tyr Arg Ser Ser Gly Ser Ile Met Thr Val Lys
                100                 105                 110

Tyr Ile Arg Glu Pro Glu His Pro Ala Ser Phe Tyr Glu Val Leu Tyr
                115                 120                 125

Phe Gln Asp Pro Gln Ala
                130

<210> SEQ ID NO 5
<211> LENGTH: 116
<212> TYPE: PRT
<213> ORGANISM: Bos taurus

<400> SEQUENCE: 5

Asp Ser Thr Asp Gly Leu Leu Val Lys Asp Lys Tyr Leu Cys Gly Asp
  1               5                  10                  15

Leu Tyr Gly Glu Glu Tyr Gly Val Ile Phe Pro Tyr Leu Gly Leu Lys
                 20                  25                  30

Thr Glu Cys Leu Trp Thr Ile Lys Met Asp Pro Leu Tyr Arg Ile Leu
                 35                  40                  45
```

-continued

```
Leu Thr Val Arg Asp Val His Glu Asn Cys Asn Lys Glu Ser Leu Glu
    50              55              60

Ile Ile Glu Gly Pro Pro Glu Ser Ser Asn Ser Arg Lys Ile Cys Asp
65              70              75                      80

Thr Ser His Ala Glu Tyr Thr Ser Cys Thr Asn Thr Met Thr Val Lys
                85              90              95

Tyr Thr Arg Lys Pro Asn His Pro Ala Pro Asp Phe Phe Leu Ile Phe
            100             105                 110

Arg Arg Val Leu
        115
```

METHODS FOR IMPROVING SPERM FUNCTIONALITY

This application is the US national phase entry of International Patent Application no. PCT/NZ2011/000019, filed Feb. 9, 2001, which claims priority to U.S. provisional patent applications Nos. 61/304,197, filed Feb. 12, 2010 and 61/424,511, filed Dec. 17, 2010.

FIELD OF THE INVENTION

This application relates to methods for enhancing the functionality of sperm. More particularly, this application relates to methods for reducing the number of sperm required in livestock artificial insemination (AI) in particular for application with flow cytometry semen sexing. The methods may also be employed to increase the fertility of sperm in some human male individuals with sub-optimal fertility.

BACKGROUND

The ability to identify and select male and female sperm has great value in the livestock industries, where there is an established market in AI of over US $2 billion per annum in the Organization for Economic Cooperation and Development (OECD) countries. This is particularly true in the dairy industry where over 80% of dairy farmers in key OECD markets impregnate their cows through artificial insemination. Sexed semen provides the opportunity to increase farmer productivity and income. For example, the availability of sexed semen has significant impact in reducing and/or eliminating the minimal returns of male dairy calves as compared to female calves.

Currently, the only commercial technique for semen sexing uses flow cytometry to sort sperm on the basis of DNA content. Bovine sperm bearing the Y chromosome have approximately 4% less DNA than sperm bearing the X chromosome. This difference, in combination with a fluorescent DNA binding dye (for example Hoechst 33342) and flow cytometry, permits purification of X chromosome bearing sperm to greater than 90% (Johnson et al., 1989). However, the ability to sort bovine sperm is currently limited to a rate of 8000 $s^{-1}$ which, when each straw, or dose, contains $2\times10^6$ sperm, translates to 14 straws/hour (Sharpe and Evans, 2009). As a result, sexed semen straws generally incorporate ten-fold less sperm than unsexed straws. In addition, the sorting process itself has a negative effect on the fertility of the sperm. The reduction in the number of sperm per straw, together with reduction in sperm fertility due to the sorting process, causes a significant reduction of 14% in the conception rate for sexed sperm compared to unsexed sperm (Frijters et al., 2009). The sexed semen also has a significant price premium over unsexed sperm due to the high cost of sorting even the sub-optimal number of sperm used in the sexed semen straws. A valuable addition to the semen sexing technology would be a method to enhance the fertility of sperm so that a dose of considerably less than the approximately $2\times10^6$ sperm per straw currently used for sexed semen would achieve the same conception rate as the normal, unsexed, straws.

Such methods would also have application in swine AI where much higher doses of sperm are used in the standard AI methodology than with bovine, namely approximately $2500\times 10^6$ sperm per straw. Recent work suggests that more sophisticated techniques involving deep intrauterine insemination can lower this requirement to 50-70 million (Vazquez et al., 2005; Vazquez et al., 2008). However, this reduced dose is still beyond the present commercial capability of flow cytometry sorted sperm.

The Sperm Journey in the Female Reproductive Tract

Sperm are highly specialized cells that deliver the haploid male genome to the haploid female genome contained in the oocyte. Despite this seemingly simple mission, the path to achieving this goal is highly complex. Extraordinarily large numbers of sperm are inseminated in a natural mating, for example approximately one billion sperm/oocyte in the cow. The inseminated sperm spend a variable period of time, ranging from hours to days in the different regions of the female reproductive tract (FRT). The environments that sperm encounter from ejaculation to fertilization of the oocyte also vary considerably. These environments range from the complex molecular mix added to sperm at ejaculation by the male to the various female secretions and different cell surfaces of the female epithelia (Drobnis and Overstreet, 1992).

Once sperm are deposited in the FRT, a combination of active sperm migration and female muscle contraction propels the sperm to the oocyte. During the journey through the FRT, sperm can be retained in specialized regions, most notably the cervix and oviduct (Drobnis and Overstreet, 1992). This retention presumably increases the probability that at least some sperm will be present in the oviduct at the same time as ovulation occurs. However, such retention may also act as a negative selection imposed against sperm by the female. The final phase of the sperm journey in the oviduct involves release of sperm from the isthmus region (controlled by the female) and travel to the ampulla for fertilization of the oocyte. At this time near unitary numbers of sperm are present (Drobnis and Overstreet, 1992). Fertilization itself is again a complex phenomena involving penetration of the cumulus oophorus and subsequently the zona pellucida (Katz et al., 1989). Although this complex journey is broadly similar between mammalian species, various aspects do differ.

Sperm also undergo a maturational change while resident in the FRT, known as capacitation. When sperm are ejaculated, they are not capable of fertilizing the oocyte. However, during passage through the FRT sperm gain the capacity to fertilize. Changes to sperm during passage through the FRT include alterations in membrane properties, enzyme activities and motility (Salicioni et al., 2007). Ultimately these changes enable sperm to respond to stimuli that induce the acrosome reaction and penetration of the egg. One of the important changes that occur during capacitation is alterations in the surface properties of sperm. A specialized protein-carbohydrate coating (Schroter et al., 1999) stabilizes the surface membrane, regulates capacitation (Topfer-Petersen et al., 1998), facilitates transport through the FRT (Tollner et al., 2008b), and enables attachment at the oviduct (Tollner et al., 2008a). In different species, essentially the same functions are carried out by the surface coatings, however the specific molecular components vary (Calvete and Sanz, 2007; Tollner et al., 2008a; Topfer-Petersen et al., 1998).

The Attrition of Sperm in the Female Reproductive Tract

In a natural bovine mating, approximately 1 billion sperm are inseminated yet less than 10,000 get to the oviduct and less than 10 get through to the oocyte (Mitchell et al., 1985). Why there are such large losses is poorly understood. Following coitis, greater than 80% of sperm are lost through vaginal discharge (Mitchell et al., 1985). The remaining sperm form a gradient in concentration from the cervix to the oviduct (Hawk, 1983; Hunter, 2003; Mitchell et al., 1985). In bovine, approximately 10,000 sperm arrive at the oviduct 6-8 hours after insemination (Mitchell et al., 1985). By 12 to 24 h after insemination, sperm have either been lost through back flushing, eliminated by phagocytosis or reached the oviduct (Hawk, 1983). In pigs, there is strong evidence for phagocytosis of sperm by polymorphonuclear neutrophils (PMNs), with a massive infiltration of PMNs occurring in the uterine lumen shortly after insemination (Matthijs et al., 2003). Recently, similar evidence that PMNs infiltrate the uterine lumen after insemination in cows has been published (Alghamdi et al., 2009).

How Sperm are Damaged During Passage Through the Female Reproductive Tract

Experimental evidence suggests that both motile and damaged (immotile and/or dead) sperm are lost by discharge (Lightfoot and Restall, 1971; Oren-Benaroya et al., 2007). In contrast, in vitro evidence indicates that live sperm are preferentially phagocytosed by neutrophils (Woelders and Matthijs, 2001). Several phenomena contribute to sperm damage from the FRT, although the mechanism and significance are poorly understood. Such phenomena include:

Adhesive properties of female epithelia capturing sperm and/or damaging the sperm surface, particularly mucus laden surfaces such as the cervix. This occurs by both biochemical and physical shearing (Katz et al., 1989; Mullins and Saacke, 1989).

Female secretions modulating and/or damaging the sperm surface or functionality such as flagella activity, capacitation and acrosome status. Such secretions include antibodies, complement components, molecular species affecting energy and osmotic homeostasis, signaling molecules particularly for capacitation, and also catabolic entities.

Sperm also cause damage to themselves through generation of reactive oxygen species (ROS) mainly as a by-product of mitochondrial function (de Lamirande and Gagnon, 1995; Koppers et al., 2008; Vernet et al., 2001). ROS cause loss of sperm motility and lipid peroxidation. The latter damage leads to alteration of the membrane properties such as flexibility and fluidity, and can also lead to lack of membrane integrity and/or decreased chromatin quality (Storey, 1997). Sperm are particularly sensitive to ROS-induced damage because of their membrane composition and their limited antioxidant defenses. In particular, the high proportion of polyunsaturated fatty acids (PUFA) in the surface membrane makes this membrane highly susceptible to oxidation (Jones et al., 1979). The nature of the sperm cell, with limited cytoplasmic fluid, also constrains the availability of intracellular antioxidants (Koppers et al., 2008, & ref within). In human sperm at least, there exists a strong relationship between ROS production and antioxidant protection for determining the lifespan of sperm in the absence of external damaging agents (Alvarez and Storey, 1985; Storey, 1997, 2008).

In summary, the FRT is hostile to sperm, in particular selecting for motile non-damaged sperm but also removing the vast majority of sperm. While in the FRT, sperm have to deal with a wide variety of physiological environments, mature particularly at the cell surface and respond appropriately to signals at the right time and place. Thus despite the sperm's simple mission and relatively simple construction, successful sperm have the characteristics of remaining undamaged (mainly a surface phenomena), not being phagocytosed, remaining motile (a function of mitochondria, glycolytic enzymes and flagella components), and being able to respond to signals appropriately (a surface phenomena but also involving signal transduction and effector pathways). Thus treatments to sperm that enhance the ability of sperm to remain undamaged, motile, not phagocytosed and functionally competent could reduce the number of sperm required for insemination.

Pegylation as a Method to Enhance Sperm Function

Polyethylene glycol (PEG) has the general formula $H(OCH_2CH_2)nOH$ with typical molecular weights of 500-20,000 daltons. It is nonimmunogenic and soluble in aqueous solutions. The polymer is nontoxic and generally does not harm active proteins or cells.

Pegylation of proteins has been shown to improve solubility and vascular longevity, and decrease the immunogenicity of xenogeneic proteins while retaining normal protein function (Abuchowski et al., 1977a; Abuchowski et al., 1977b; Jackson et al., 1987; Senior et al., 1991; Zalipsky et al., 1994). Pegylation has also been used directly on cells to provide immune camouflage, initially for transfusion of red blood cells (Chen and Scott, 2001; Scott et al., 1997) and subsequently for other tissues such as pancreatic beta islet cells (Chen and Scott, 2001; Teramura and Iwata, 2009). For both red blood cells and pancreatic beta islet cells, the respective cell functions were preserved despite the pegylation. As the main loss of sperm within the FRT is by phagocytosis it may be possible to pegylate the sperm for protection while still preserving function.

SUMMARY OF INVENTION

The present disclosure provides methods and compositions for improving the functionality and/or fertility of sperm, for example by enhancing motility, protecting against phagocytosis by neutrophils and extending the lifespan of sperm in the FRT. Pegylation of sperm may also have value in improving in vitro fertilization rates and also quality of blastocyts. The disclosed methods and compositions may be used in artificial insemination, for example, to reduce the number of sperm needed for insemination and to improve conception rates.

In one aspect, the disclosed methods comprise adding a polyethylene glycol (PEG), such as monomethoxy-poly(ethylene glycol) (mPEG) to the surface of sperm by contacting the sperm with an effective amount of a composition comprising a pegylated binding agent, wherein the binding agent is capable of binding to the sperm. In certain embodiments, the binding agent is a seminal plasma protein. In compositions for use with bovine sperm, for example, seminal plasma proteins that can be effectively employed include, but are not limited to, PDC-109, BSP-A3, BSP-30 kDa, aSFP, Z13 and clusterin. Other binding agents that can be effectively employed in the disclosed compositions include antibodies, such as monoclonal antibodies or antigen-binding fragments thereof, that specifically bind to a seminal plasma protein. Additional sperm binding agents include lectin molecules that recognize carbohydrates on the sperm surface, antibodies to sperm antigens, and also egg yolk that is used for extending bovine sperm and that has proteins that bind to bovine sperm.

In other embodiments, a PEG, such as mPEG, is added to the surface of sperm by contacting the sperm with an effective amount of a composition comprising a PEG molecule with a reactive group that conjugates directly to the sperm surface. For example, PEG with an amine reactive group can covalently attach to sperm surface proteins.

In other embodiments, a PEG, such as mPEG, is added to the surface of sperm by contacting the sperm with an effective amount of a composition comprising a pegylated membrane anchoring agent. In certain embodiments, the membrane anchoring agent is a lipid such as, but not limited to, cholesterol, diacylglycerolipid, dialkylglycerolipid, glycerophospholipid, sphingosine derived diacyl- or dialkyl lipid, ceramide, phosphatidate, phosphatidyl choline, phosphatidyl ethanolamine, phosphatidyl serine, phosphatidyl inositol or phosphatidyl glycerol.

In another aspect, methods for improving the functionality and/or fertility of sperm are provided that comprise contacting the sperm with a lipid-PEG-functional moiety conjugate, wherein the functional moiety is effective in improving the functionality and/or fertility of the sperm.

In a further aspect, the present disclosure provides methods for making a preparation for use in AI or in vitro fertilization, such methods comprising obtaining sperm from a mammal, optionally separating the sperm into X chromosome-bearing and Y chromosome-bearing sperm, and contacting the sperm with an effective amount of a composition and/or construct disclosed herein. Methods for separating X chromosome-bearing sperm from Y chromosome-bearing sperm are known to those of skill in the art, and include, for example, flow cytometry. Such methods include, but are not limited to, those described in U.S. Pat. Nos. 5,135,759, 5,985,216, 6,149,867 and 6,263,745.

In yet another aspect, preparations for use in AI or in vitro fertilization are provided, such preparations comprising live sperm and a composition and/or construct disclosed herein. In certain embodiments, the sperm bear the X chromosome.

Methods for the cryopreservation of sperm are also provided by the present disclosure. Such methods comprise: (a) contacting the sperm with a cryoprotectant and an effective amount of a composition and/or construct disclosed herein, and (b) storing the sperm and the composition/construct at a temperature of about 4° C. to about −196° C., wherein the effective amount of the composition is sufficient to increase the functionality and/or fertility of the sperm relative to sperm stored without the composition/construct. Examples of cryoprotectants that can be effectively employed in such methods include, but are not limited to, PEG, dimethyl sulfoxide (DMSO), ethylene glycol, propylene glycol, polyvinylpyrrolidone (PVP), polyethylene oxide, raffinose, lactose, trehalose, melibiose, melezitose, mannotriose, stachyose, dextran, hydroxy-ethyl starch, sucrose, maltitol, lactitol and glycerol. In related aspects, preparations comprising cryogenically preserved sperm and a composition and/or construct disclosed herein are provided. Methods for cryopreserving sperm are well known in the art and include those disclosed, for example, in U.S. Pat. No. 7,208,265 and U.S. Patent Application Publication No. US 2007/0092860.

The methods, compositions and constructs disclosed herein are particularly advantageous in the preparation of semen for use in AI of mammals including, but not limited to, cows, pigs, sheep, goats, humans, camels, horses, deer, alpaca, dogs, cats, rabbits and rodents. Semen used in such methods may be either fresh ejaculate or may have been previously frozen and subsequently thawed.

These and additional features of the present invention and the manner of obtaining them will become apparent, and the invention will be best understood, by reference to the following more detailed description.

DETAILED DESCRIPTION

As outlined above, the present disclosure provides methods for improving the functionality and/or fertility of sperm, together with compositions and constructs for use in such methods. In certain embodiments, the methods and compositions disclosed herein enhance motility, protect sperm from phagocytosis and/or extend the lifespan of sperm in the FRT. The ability of a composition or construct to increase the functionality and/or fertility of sperm may be determined by contacting sperm with the composition or construct; measuring parameters such as the motility, resistance to neutrophil attack, membrane integrity and/or presence of sperm surface markers indicative of capacitation and acrosome status on the treated sperm and ability to recover from cryopreservation; and comparing the results with those obtained for untreated sperm. The functionality of modified sperm can also be determined by investigating their interaction with cervical explants or synthetic analogues, and/or their ability to capacitate, acrosome react and fertilize in vitro. Techniques for measuring the above parameters are well known in the art and include those described below. In certain embodiments, the disclosed methods comprise adding a PEG, such as mPEG, to the surface of either sorted or unsorted sperm.

Role of Sperm Surface Proteins in the Fertility and/or Functionality of Sperm

After ejaculation, sperm are bathed in seminal plasma made up of secretions from testes, epididymis and the accessory sex glands (Calvete and Sanz, 2007; Maxwell et al., 2007). The seminal plasma is a complex mixture composed of amino acids, lipids, fatty acids, osmolytes, membrane vesicles, peptides and proteins (Calvete and Sanz, 2007; Maxwell et al., 2007). Proteins from the seminal fluid have been shown to be associated with fertility in the bull (Killian et al., 1993) and comparison of levels of these proteins between high and low fertility bulls indicates that four of these proteins can account for approximately 50% of the variation between the two groups of bulls (Moura et al., 2006). Several of these proteins, and others added during sperm epidymal transit, have been shown to bind to specific regions of sperm and possess distinct ligand binding capabilities. Such sperm surface proteins have been shown to have activities that modulate sperm viability (Centurion et al., 2003), motility (Garcia et al., 2006), uterine immune activity (Calvete and Sanz, 2007; Einspanier et al., 1991), penetration of cervical mucus (Tollner et al., 2008b), capacitation state (Manjunath and Therien, 2002; Therien et al., 1997; Tollner et al., 2009), and both oviduct (Ekhlasi-Hundrieser et al., 2005; Tollner et al., 2008a; Yamaguchi et al., 2009) and zona pellucida binding (Dostalova et al., 1995), and provide immune protection (Yudin et al., 2005). Collectively these studies strongly suggest that the surface of the sperm has an important role in the regulation of sperm fertility.

In the ungulates (i.e. pig, bull, ram and stallion), components from the ejaculate, particularly proteins from the accessory sex glands, bind to the sperm surface and inhibit capacitation (known as decapacitation; (Maxwell et al., 2007)). Several of these decapacitating factors are sourced from the major seminal plasma proteins and belong to the spermadhesin and fibronectin-type II (FN2) choline binding protein families (Calvete and Sanz, 2007). However, the precise role of the majority of seminal fluid proteins is unknown and there are significant differences between species both in the protein composition of seminal plasma and the apparent function of proteins from the same protein family (Calvete and Sanz, 2007; Manjunath et al., 2007). Despite these differences, the membrane remodeling events, such as loss of surface bound proteins and lipids upon capacitation of sperm in the FRT, are essentially conserved across mammalian species (Calvete and Sanz, 2007; Tollner et al., 2009) The surface of sperm is an important feature of sperm fertility since it is the site of damage from some female reproductive secretions and also the site for retention or damage from epithelia and immunological attack. Thus enhancing the surface characteristics to reduce surface retention or damage may increase sperm fertility. However, the sperm surface is also the site for interaction of sperm with both soluble signals from the FRT and specific tissue binding to the FRT. Examples of soluble signals involved in such specific interactions include the molecules glycosaminoglycan (GAG) and high density lipoprotein (HDL), which are both involved in triggering capacitation in the cow (Lane et al., 1999; Therien et al., 2005; Therien et al., 1995; Therien et al., 1998). Examples of sperm-tissue interaction include that of the sperm with the uterotubal-junction (Yamaguchi et al., 2009) and binding to the oviductal epithelia (Gwathmey et al., 2006). Thus overall, a balance for sperm surface enhancement, that adds protection to sperm but enables specific signaling and binding to occur, needs to be found. One attractive means to achieve this goal is to add the protectant to the decapacitating factors that coat sperm and that are lost upon capacitation.

The inventors believe that mPEG is able to act as such a protectant. Covalent linking of mPEG (known as pegylation) to a drug (Greenwald et al., 2003) or therapeutic protein (Roberts et al., 2002) masks the molecule from the host's immune system and increases the hydrodynamic size of these agents. Thus pegylation prolongs circulatory time of the parent molecule by reducing renal clearance and increasing the resistance to proteolysis (Harris and Chess, 2003). Pegylation has also been used to immunocamouflage cells, in particular for blood transfusion, a specialized cell transplantation where pegylation can significantly diminish rejection episodes (Chen and Scott, 2001). Pegylation and transplantation studies have also been carried out on isogenic rat pancreatic islets to demonstrate that pegylation does not impair in vivo cellular signaling and function (Chen and Scott, 2001).

The major protein fraction (50-70%) of bovine seminal plasma is represented by a family of phospholipid-binding proteins collectively called BSP proteins (Manjunath et al., 2007). The BSP protein signature is characterized by the presence of the FN2 domains (Manjunath et al., 2007). Specifically each BSP is composed of a unique N-terminal domain followed by two FN2 domains in tandem that are separated by a short linker polypeptide chain (Constantine et al., 1992; Wah et al., 2002). The BSP FN2 domains have been shown to contain a choline phospholipid-binding site (Calvete et al., 1996; Desnoyers and Manjunath, 1992) and, on other surfaces, binding sites for heparin (Calvete et al., 1996; Chandonnet et al., 1990) and HDL (Therien et al., 1997). In bovine seminal plasma, three FN2 family members are present at the following concentrations (Nauc and Manjunath, 2000): BSP-A1/A2 (also known as PDC-109, present at 15-20 mg/ml), BSP-A3 (present at 2-4 mg/ml), and BSP-30 kDa (present at 4-6 mg/ml). Upon ejaculation, the BSPs bind to sperm membranes and play a crucial role in GAG/HDL-mediated surface modification that occurs during capacitation (Therien et al., 1998; Therien et al., 1997). The BSP proteins are lost from the surface of sperm during capacitation (Therien et al., 2001).

In bovine seminal fluid, the major spermadhesin protein is the acidic seminal fluid protein (aSFP), a 114 residue, non-glycosylated protein present at 2-7 mg/ml in seminal plasma (Dostalova et al., 1994; Wempe et al., 1992). This protein binds loosely to the surface of sperm and is quantitatively released during in vitro capacitation (Dostalova et al., 1994). The protein may have a role in oxidation protection and may also stimulate lymphocytes and endometrial progesterone secretion (Einspanier et al., 1991). A second spermadhesin, known as Z13, is also present in seminal plasma. This protein is also non-glycosylated but is present as a dimer, and at a concentration of approximately 0.5 mg/ml (Tedeschi et al., 2000).

The proteins that bind to the surface of the sperm appear to be, highly variable between species. In addition, the site of transfer to the sperm is also variable. For example in the mouse and monkey, beta defensins appear to have the role of decapacitation factors (Tollner et al., 2009; Yudin et al., 2008). Also in the mouse, these proteins are not added after ejaculation but coat the sperm during their transit through the epididymis (Yudin et al., 2008). In the human, bovine BSP-like genes are present, however their expression as proteins in seminal fluids is as a very minor component (Lefebvre et al., 2007). Another family of proteins that is associated with the sperm surface and that can be released by capacitation are the CRISPs, a family of proteins characterized by sixteen invariant cysteine residues (Topfer-Petersen et al., 2005). In the human, the eppin (also known as SPINLW1; serine peptidase inhibitor-like with Kunitz and WAP domains 1) and CD52 molecules may act as a decapacitation factor (Focarelli et al., 1999; Focarelli et al., 1998; Focarelli et al., 1995). One protein that appears to be present on the sperm surface of many species is clusterin (see Table 1);

Addition of Polyethylene Glycol to Sperm Surface

In one aspect, the methods disclosed herein involve adding the protectant PEG to sperm using techniques that provide protection but at the same time allow sperm to maintain the array of molecular and cellular interactions that occur in ascent through the FRT, and thereby increase the functionality and/or fertility of the sperm. In certain embodiments, such methods employ compositions including a PEG, such as mPEG, and a binding agent that binds, either directly or indirectly, to the cell surface of sperm.

PEGs having a wide range of molecular weights can be effectively employed in the disclosed methods. For example, in certain embodiments the PEG has a molecular weight in the range of about 200 to about 40,000 daltons. PEGs contemplated for use in the methods, compositions and constructs disclosed herein include, but are not limited to, mPEG, monoalkyl-substituted PEGs, PEGs having one or more amine reactive groups that allow conjugation to a protein, and include linear and branched chain PEGs. Cholesterol-PEG derivatives that can be effectively employed in the disclosed methods, compositions and constructs are available commercially and include those available from NOF Corporation (White Plains, N.Y.).

In one embodiment, the binding agent is a protein that is known to bind to sperm and be lost upon capacitation. In the bovine these include, for example, PDC-109 (NCBI Accession NP_001001145.1; SEQ ID NO: 1), BSP-A3 (NCBI Accession NP_777265.1; SEQ ID NO: 2), BSP-30 kDa (NCBI Accession NP_777267; SEQ ID NO: 3), aSFP (NCBI accession NP_777041.1; SEQ ID NO: 4) and Z13 (NCBI Accession P82292; SEQ ID NO: 5). Additional potential seminal plasma proteins that associate with sperm and that can be used for pegylation are shown below in Table 1.

TABLE 1

| SPECIES | FIBRONECTIN TYPE II DOMAINS | CUB DOMAINS (spermadhesin) | BETA DEFENSINS | CRISPS | OTHERS |
|---------|------------------------------|----------------------------|----------------|--------|--------|
| Bovine | PDC-109, BSP-A3, BSP-30 kDa | aSFP, Z13 | | Crisp1 & Crisp3 present in semen, and Crisp2 on sperm (our proteomics results) | Clusterin (Howes et al., 1998) |

TABLE 1-continued

| SPECIES | FIBRONECTIN TYPE II DOMAINS | CUB DOMAINS (spermadhesin) | BETA DEFENSINS | CRISPS | OTHERS |
|---|---|---|---|---|---|
| Swine | pB1 (Manjunath et al., 2007) | AWN, AQN-1, AQN-3, PSP-1, PSP-II | | Probable PMID: 18716287 | |
| Equine | HSP-1 & HSP-2 (Topfer-Petersen et al., 2005a) | HSP-7 (Topfer-Petersen et al., 2005a) | | Crisp1 & Crisp2 (Giese et al., 2002); Crisp3 (Topfer-Petersen et al., 2005b) | |
| Human | BSPH1 (Lefebvre 2009) | | BD126 (Liu et al., 2001) | | CD52 (Flori et al., 2008); Eppin, (Wang et al. 2003); Clusterin (Wang et al., 2007) |
| Murine | | | BD22 (Yudin et al., 2008) | Crisp1 (Nixon et al., 2006) | PBP & DF10 (Nixon et al., 2006); Eppin (Sivashanmugam et al., 2003); Clusterin (Baker et al., 2008b; Stein et al., 2006) |
| Rat | | | 2d6 (Jones and Brown, 1987) | Crisp1 (Roberts et al., 2007) | CD52 (Derr et al., 2001), Clusterin (Baker et al., 2008a) |
| Monkey (Macaque) | | | BD126 (Yudin et al., 2005b) | | |

In another embodiment, the binding agent is a molecule that binds to a seminal protein that is itself known to bind to sperm and be lost upon capacitation. Examples of such molecules include lectins and antibodies and antigen-binding fragments thereof that bind to seminal plasma proteins, and proteins known to bind to sperm such as chicken egg yolk proteins including vitellogenins and apolipoprotein B. In the bovine, for example, such antibodies include those that specifically bind to PDC-109, BSP-A3, BSP-30 kDa, aSFP and/or Z13 (see, for example Manjunath and Sairam, 1987; Nauc and Manjunath, 2000). Lectins that show significant binding to bovine or swine sperm include those listed in Table 2 below.

TABLE 2

| LECTIN | REACTIVE SPECIES | REFERENCES |
|---|---|---|
| WGA (*Triticum vulgaris* lectin; wheat germ agglutinin) | Bovine, swine | 1, 2 |
| Con-A (Concanavalin A) | Bovine, swine | 1, 2 |
| UEA (*Ulex europus* agglutinin) | Swine | 1 |
| PNA (Peanut agglutinin) | Bovine | 2, 3 |
| SBA (Soybean agglutinin) | Bovine, swine | 2, 4 |
| MAA-I (*Maackia amurensis* agglutinin) | Bovine | 2 |
| ECA (ECL; *Erythrina cristagalli* lectin) | Bovine, swine | 2, 4 |
| VVL (*Vicia villosa* lectin) | Bovine | 5 |
| RCA I (*Ricinus communis* agglutinin) | Bovine | 5 |

Reference key: 1: (Jimenez et al., 2003), 2: (Taitzoglou et al., 2007), 3: (Cross and Watson, 1994), 4: (Ashworth et al., 1995), 5: Inventors' data.

The binding agents disclosed herein are pegylated using techniques well known to those of skill in the art, such as those described in (Kodera et al., 1998; Roberts et al., 2002). The pegylated binding agent is then added to sperm (either sexed or unsexed) prior to AI.

In other embodiments, a PEG is attached to sperm using a membrane anchoring agent. As used herein, the term "membrane anchoring agent" refers to a molecule that is known to spontaneously and stably incorporate into lipid bilayers, including cell membranes. Examples of such molecules include, but are not limited to, the synthetic molecules described in U.S. Patent Publication No. US 2007/0197466, the disclosure of which is hereby incorporated by reference. In certain embodiments, the membrane anchoring agent is a lipid. Lipids that may be effectively employed in the disclosed methods include, but are not limited to, diacyl- and dialkyl-glycerolipids, including glycerophospholipids and sphingosine derived diacyl- and dialkyl lipids, including ceramide. In certain embodiments, the lipid is selected from the group consisting of: cholesterol, diacylglycerolipids, phosphatidate, phosphatidyl choline, phosphatidyl ethanolamine, phosphatidyl serine, phosphatidyl inositol and phosphatidyl glycerol. The lipid may be derived from one or more cis-desaturated fatty acids.

The lipid can be linked to a PEG either directly or by a linker, such as —$CO(CH_2)_3CO$—, —$CO(CH_2)_4CO$ or —$CO(CH_2)_5CO$—. PEG phospholipid conjugates that can be effectively employed in the disclosed methods include those available from Avanti Polar Lipids, Inc. (Alabaster, Ala.). The pegylated membrane anchoring agent is added to sperm prior to AI.

In other embodiments, PEG is attached to sperm through an amine reactive group directly to sperm surface proteins, as described below in Example 7.

Polypeptides and Proteins

Proteins and/or polypeptides employed in the disclosed methods, compositions and constructs can be isolated from sperm using techniques well known to those of skill in the art, such as those described in Manjunath and Sairam (1987). Alternatively, such proteins and/or polypeptides can be prepared recombinantly by inserting a polynucleotide that encodes the protein into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, mycobacteria, insect, yeast or a mammalian cell line such as COS or CHO.

The conjugates and compositions disclosed herein encompass variant polypeptide sequences that have been modified by one or more amino acid deletions, additions and/or substitutions. Variant sequences preferably exhibit at least 75%, more preferably at least 80%, more preferably at least 85%, more preferably at least 90%, more preferably yet at least 95%, and most preferably at least 98% identity to a specific polypeptide sequence disclosed herein. The percentage identity is determined by aligning the two sequences to be compared as described below, determining the number of identical residues in the aligned portion, dividing that number by the total number of residues in the inventive (queried) sequence, and multiplying the result by 100. In addition to exhibiting the recited level of sequence identity, variant sequences preferably exhibit a functionality that is substantially similar to the functionality of the specific sequences disclosed herein. Preferably a variant polypeptide sequence will have at least 80%, more preferably at least 85%, more preferably at least 90%, more preferably yet at least 95%, and most preferably 100% of the sperm fertility enhancing activity possessed by the specifically identified polypeptide sequence in sperm fertility assay, such those described below. Such variants may generally be identified by modifying one of the polypeptide sequences disclosed herein, and evaluating the properties of the modified polypeptide or fusion polypeptide using, for example, the representative procedures described herein.

In certain embodiments, variant sequences differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, tip, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide in the conjugate.

Polypeptide sequences may be aligned, and percentages of identical amino acids in a specified region may be determined against another polypeptide, using computer algorithms that are publicly available, such as the BLASTP algorithm. BLASTX and FASTX algorithms compare nucleotide query sequences translated in all reading frames against polypeptide sequences. The use of the BLAST family of algorithms is described at NCBI's website and in the publication of Altschul et al. The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

All of the polypeptides described herein are isolated and purified, as those terms are commonly used in the art. Preferably, the polypeptides are at least about 80% pure, more preferably at least about 90% pure, and most preferably at least about 99% pure. Various techniques suitable for achieving such purification are well known to those of skill in the art. These include, for example, precipitation with ammonium sulfate, PEG, antibodies and the like, or by heat denaturation, followed by centrifugation; chromatography steps such as ion exchange, gel filtration, reverse phase, hydroxylapatite and affinity chromatography; isoelectric focusing; gel electrophoresis; and combinations of these and other techniques.

Antibodies

Antibodies that specifically bind a seminal plasma protein can be prepared by any of a variety of techniques known to those of ordinary skill in the art. See, e.g., (Harlow and Lane, 1988). In general, antibodies can be produced by cell culture techniques, including the generation of monoclonal antibodies, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (Kohler and Milstein, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816, 567. DNA encoding the monoclonal antibodies may be isolated and sequenced using conventional procedures. Recombinant antibodies, antibody fragments, and fusions and polymers thereof, can be expressed in vitro in prokaryotic cells (e.g. bacteria) or eukaryotic cells (e.g. yeast, insect or mammalian cells) and further purified as necessary using well known methods.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., 2000; Krebs et al., 2001) U.S. Pat. No. 6,300, 064). A method for construction of human combinatorial libraries useful for yielding functional Fab fragments has been described by Rauchenberger et al. (Rauchenberger et al., 2003)

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Ehrlich et al., 1980; Hochman et al., 1976; Inbar et al., 1972)

A wide variety of expression systems are available in the art for the production of antibody fragments, including Fab, single-chain variable fragment (scFv), $V_L$ and $V_H$. For example, expression systems of both prokaryotic and eukaryotic origin may be used for the large-scale production of antibody fragments and antibody fusion proteins. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins. Yeasts and filamentous fungi are accessible for genetic modifications and the protein of interest may be secreted into the culture medium. In addition, some of the products comply with the GRAS (Generally Regarded as Safe) status in that they do not harbor pyrogens, toxins, or viral inclusions.

Methylotrophic and other yeasts such as *Candida boidinii*, *Hansenula polymorpha*, *Pichia methanolica*, and *Pichia pastoris* are well known systems for the production of heterologous proteins. High levels of proteins, in milligram to gram quantities, can be obtained and scaling up to fermentation for industrial applications is possible.

The *P. pastoris* system is used in several industrial-scale production processes. For example, the use of *Pichia* for the expression of scFv fragments as well as recombinant antibodies and fragments thereof, has been described (Andrade et al., 2000; Pennell and Eldin, 1998; Ridder et al., 1995) In shake-flask cultures, levels of 250 mg/L to over 1 g/L of scFv can be achieved (Eldin et al., 1997; Freyre et al., 2000)

Similar expression systems for scFv have been described for *Saccharomyces cerevisiae*, *Schizosaccharomyces pombe*, *Yarrowia lipolytica*, and *Kluyveromyces lactis*. (Davis et al., 1991; Horwitz et al., 1988; Swennen et al., 2002) Filamentous fungi, such as *Trichoderma* and *Aspergillus*, have the capacity to secrete large amounts of proteins. This property may be exploited for the expression of scFv and $V_{HH}s$ (variable domain of heavy chain antibodies). (Durand and Clanet, 1988; Gouka et al., 1997; Keranen and Penttila, 1995; Nevalainen et al., 1994; Nyyssonen et al., 1993; Punt et al., 2002; Radzio and Kuck, 1997; Verdoes et al., 1995; Ward et al., 1990) and Nyyssonen et al., International Patent Publication no. WO 92/01797.

Methods

In certain embodiments of the disclosed methods, sperm are collected by artificial vagina and are immediately purified by a single density layer (Percoll™ PLUS, GE Healthcare, see protocol below). Sperm are then incubated in a suitable media with an effective amount of one or more of the compositions and/or constructs disclosed herein for a short period of time, followed by the addition of a suitable extender to enable immediate use or freezing. Alternatively the compositions and/or constructs are added directly to the ejaculate. After slight dilution, a short incubation (15-30 minutes) and the addition of extender, the resulting mixture is either cooled or frozen for future use. In another method the compositions and/or constructs may be added to extended semen. In other embodiments, sperm are sexed by flow cytometry and are collected in a media containing an effective amount of one or more of the disclosed compositions and/or constructs. Alternatively, once sufficient sorted sperm are collected, the composition and/or construct is added and incubated in a suitable media for a short period of time, followed by the addition of extender and then either immediate use or freezing.

As used herein, the term "effective amount" of a composition and/or construct disclosed herein refers to that amount sufficient to enhance sperm motility, protect sperm from phagocytosis and/or extend the lifespan of sperm in the FRT, by at least 5-50% compared to untreated sperm.

Those of skill in the art will appreciate that for use in the disclosed methods, the compositions and constructs disclosed herein may be present in compositions including one or more physiologically acceptable carriers or diluents, such as water or saline. Such compositions may additionally contain other components, such as preservatives, stabilizers, buffers and the like. Carriers, diluents and other components suitable for use in the present compositions are well known to those of skill in the art and include those currently used in preparations for AI.

All U.S. patents, U.S. patent application publications, U.S. patent applications, foreign patents, foreign patent applications, non-patent publications, tables, sequences, webpages, or the like referred to in this specification, are incorporated herein by reference, in their entirety. The following examples are intended to illustrate, but not limit, this disclosure.

Example 1

Purification of Seminal Plasma Proteins

Bovine ejaculate without extender was collected from multiple bulls, pooled and centrifuged at low speed 1,500 g for 15 min to remove the sperm cells. The supernatant was re-centrifuged at 15,000 g for 15 min and the clarified supernatant (Seminal Plasma; SP) was retained and used for isolation of SP proteins.

PDC-109

PDC-109 was purified by ion exchange chromatography as follows. SP was dialyzed into 1M NaCl, 25 mM Tris-HCl pH 6.4 and loaded onto a 20 mL-HiPrep DEAE FF 16/10 column pre-equilibrated with 1M NaCl, 25 mM Tris-HCl pH 6.4. The column was washed with 1M NaCl, 25 mM Tris-HCl pH 6.4 and the protein eluted in a single step with 1M NaCl, 25 mM Tris-HCl pH 6.4, 10 mM phosphocholine. This process resulted in a yield of approximately 13 mg of purified PDC-109/mL of SP with greater than 95% purity.

BSP-30 kDa

BSP-30 kDa was purified in two stages using gel filtration chromatography followed by ion-exchange chromatography. Specifically, SP was diluted 1:2 in equilibration buffer (50 mM Tris-HCl pH 7.4, 150 mM NaCl) and loaded onto a 320 mL-HiPrep 26/60 Sepharcyl S-200 gel filtration column. Proteins were eluted isocratically in 50 mM Tris-HCl pH 7.4, 150 mM NaCl. SDS-PAGE was utilized to determine the fraction containing the BSP-30 kDa protein. The eluted fraction containing BSP-30 kDa protein was dialyzed into 1M NaCl, 25 mM Tris-HCl pH 6.4 and purified as described for PDC-109. This process resulted in a yield of approximately 6 mg of purified BSP-30 kDa/mL of SP with greater than 95% purity.

BSP-A3

BSP-A3 was purified using gel filtration chromatography as described above for BSP-30 kDa. SDS-PAGE was utilized to determine the fraction containing the BSP-A3 protein. This process resulted in a yield of approximately 6 mg of purified BSP-A3/mL of SP with greater than 95% purity.

aSFP aSFP was purified in two stages, namely gel filtration chromatography followed by anion exchange chromatography. Gel filtration chromatography was conducted as described for isolation of the BSP-30 kDa protein. Following SDS-PAGE analysis to determine the fraction containing the aSFP, the selected fraction was then purified further by anion exchange chromatography. The eluted fraction containing aSFP was dialyzed into binding buffer (6 mM Tris-HCl pH7.4) and loaded onto a 20 mL-HiPrep DEAE FF 16/10 column. aSFP was eluted using a linear gradient of 6 mM Tris-HCl pH7.4, 1M NaCl. This process resulted in a yield of approximately 1.5 mg of purified aSFP/mL of SP with greater than 95% purity.

Example 2

Generation of Antibodies to Seminal Plasma Proteins

Ten to sixteen week old Flemish Giant rabbits (2.5-3 kg) were utilized for the generation of antibodies to the purified SP proteins. After purification, SP proteins were lyophilized to a concentration of approximately 1 mg/mL and then dialyzed into PBS. Rabbits were injected every two weeks for a total of 8 weeks with 200 ug of protein mixed with 1 ml of Freund's complete adjuvant for the initial immunization and mixed with Freund's incomplete adjuvant for subsequent immunizations. One week after the last immunization, rabbits were euthanized and blood collected by cardiac puncture. Serum antibody titers to the respective proteins were evaluated using ELISA and all animals developed titers greater than 15,000 to the respective seminal plasma proteins PDC-109, BSP-30 kDa, BSP-A3 and aSFP, as measured by end-point dilution.

Example 3

Preparation and Testing of Pegylated Seminal Plasma Proteins a) Pegylation of Seminal Plasma Proteins NHS-dPEG$_4$-Biotin was resuspended in H$_2$O. Two hundred micrograms of PDC-109, BSP-A3, BSP-30 kDa and aSFP, were mixed in molar ratios of 1:5, 1:20, 1:40 and 1:60 with NHS-dPEG$_4$Biotin and incubated for 30 min at room temperature. The reaction was stopped by the addition of 1M Tris-HCl pH7.4 at a final concentration of 25 mM. Pegylated proteins were dialysed against PBS to remove excess PEG. Pegylation was assessed by SDS-PAGE with Coomassie Blue staining. SDS-PAGE of the reacted proteins indicated that increasing molar ratios of NHS-dPEG$_4$-Biotin to seminal fluid protein resulted in increasing molecular weight, strongly suggesting pegylation. Western blots with labelled streptavidin supported this conclusion.

b) Fluorescence Microscopy Showing Pegylated Seminal Proteins Binding to Sperm

Bovine sperm cells from liquid extended semen were percoll-purified and washed in non-capacitating media (NCM; Table 3 below) with addition of 0.1% PEG (MW 600, Serva). The cells were incubated with pegylated/biotinylated SP proteins in NCM at 37° C. for 30 min, and centrifuged once to remove the supernatant. Cell pellets were resuspended in NCM containing streptavidin-alexa fluor 488 and LIVE/DEAD fixable far red dye, and incubated at 37° C. for 1 hr. Cells were washed once in NCM, and resuspended in NCM to a final concentration close to 10$^7$ cells/ml. DAPI was added to cells, and 10$^5$ cells were placed onto Superfrost plus slide. The sperm cells were studied with a Leica DMRE microscope equipped with a Leica DC500 camera, a fluorescent ebq 100 lamp and interchangeable filter sets. Cells incubated with biotinylated PDC-109 or aSFP showed strong fluorescent signal in the acrosomal cap part of sperm head.

TABLE 3

| 1X NCM (non-capacitating media, pH 7.4) | |
| --- | --- |
| Component | Concentration |
| NaH$_2$PO4 | 0.3 mM |
| KCl | 3.1 mM |
| MgCl$_2$ | 0.4 mM |
| Sodium pyruvate | 1 mM |
| HEPES | 40 mM |
| NaCl | 100 mM |
| Lactate (85%) | 21.7 mM |
| Gentamicin | 50 µg/ml | c) Flow Cytometry Showing Pegylated Seminal Proteins Binding to Sperm

Sperm cells were prepared by centrifugation of fresh ejaculate containing extender through a 60% Percoll™ PLUS gradient followed by one wash in NCM. The sperm cells were then incubated for 30 min at 28° C. with 1 µg/mL of each of the pegylated SP proteins. After incubation with the pegylated SP proteins, cells were washed once, streptavidin-alexa fluor 488 was added to the cells and they were incubated for a further 30 min at 37° C. Flow cytometry analysis was then conducted. Both PDC-109 and BSP-A3 demonstrated binding to sperm cells as indicated by a right-shift in the histogram when compared to the control cells incubated with streptavidin-alexa fluor 488 alone.

Example 4

Sperm Maturation Model

In this model, as detailed below, bovine sperm are incubated overnight in NCM under non-capacitating conditions (simulating the conditions sperm experience for the majority of the journey in the FRT, starting cell viability approximately 90%). Following overnight incubation, sperm are diluted in capacitating media (CM; Table 4), triggering capacitation with high efficiency and minor loss of viability (cell viability in the 75-85% range). In typical experiments, when bovine sperm are capacitated with caffeine, db-cAMP and IBMX (3-isobutyl-1-methylxanthine), greater than 95% of viable cells capacitate as assessed by WGA-fluorescein/Annexin V or merocyanine 540 binding (see Table 5; WGA staining is the most sensitive, with approximately 10-fold shift in the staining upon capacitation). When cells are capacitated in vitro they also gain the capacity to acrosome react (Table 5). Although the combination of caffine, db-cAMP and IBMX is an efficient inducer of capacitation, when more in vivo like capacitation induction is required, heparin is used. Pegylated sperm are compared with unpegylated sperm for their ability to mature, in particular using heparin induction method.

TABLE 4

| 1X CM (capacitating media, pH 7.4) | |
| --- | --- |
| Component | Concentration |
| NaH$_2$PO$_4$ | 0.3 mM |
| KCl | 3.1 mM |
| MgCl$_2$ | 0.4 mM |
| Sodium pyruvate | 1 mM |
| HEPES | 20 mM |
| NaCl | 100 mM |
| Lactate (85%) | 21.7 mM |
| NaHCO$_3$ | 60 mM |
| CaCl$_2$ | 3.9 mM |
| Gentamicin | 50 µg/ml |
| Fatty acid-poor BSA | 2 mg/ml |

TABLE 5

| CHARACTERISTIC | ASSAY | NOTES | REFERENCES |
|---|---|---|---|
| Motility & morphology | Qualisperm and Bright field microscopy | Enables quick quantitative motility analysis for 1000s of cells. Can also indicate capacitation (hypermotility) | (Tejerina et al., 2008) |
| Viability/Membrane integrity | Flow cytometry (FC)/ Fluorescent microscopy (FM) using a range of dyes including Propidium iodide, Yo pro-1, Hoechst 33258 (H33258), LIVE/DEAD fixable far red and SYBR 14 | Depending upon the experiment, different vital dyes are used depending upon their properties (all available from Invitrogen). These dyes are used alone but also in combination with other FC assays described below. Overall allows quantification of cells with permeant membranes | See (Gillan et al., 2005), for a review and references within |
| Shape and granularity | FC/FM | Enables quantification of size and cellular aggregation changes | (Gillan et al., 2005) |
| Mitochondrial function/membrane potential | FC/FM with JC-1 or DilC1(5) (Invitrogen) | The DilC1(5) dye is a member of the cationic cyanine dyes that have been shown to accumulate in cells in response to membrane potential and thus permits quantification of mitochondrial functionality change | (Shapiro et al., 1979) |
| Capacitation status | FC in combination with WGA-fluorescein (Invitrogen)/Annexin V-fluorescein/ merocyanin 540 binding as quantified by flow cytometry. Also the ability to undergo acrosome reaction is used as a measure of capacitation | Capacitation induces sperm surface changes, WGA/Annexin V and merocyanin 540 all enable quantification of capacitation changes | (Gadella and Harrison, 2002; Mahmoud and Parrish, 1996; Medeiros and Parrish, 1996; Rathi et al., 2001) |
| Acrosome integrity | FC in combination with PNA-647 (Invitrogen)/SBTI (Soyabean trypsin inhibitor)-488 (Invitrogen) | Both PNA and SBTI allow quantification of changes on the sperm acrosome surface that reflect acrosome reaction, although this assay is generally used to monitor spontaneous acrosome reaction. The ability of cells to acrosome react when initiated by calcium ionophore A23187 is also used as a measure of capacitation | (Harper et al., 2008; Nagy et al., 2003) |
| Surface antibody binding | FC/FM in combination with antibodies | As discussed above, we have developed polyclonal antibodies to four seminal plasma proteins on bovine sperm (PDC-109, BSP-A3, BSP-30 kDa, aSFP). These allow quantification of changed antibody recognition of pegylated proteins and also changes on the surface of sperm by direct pegylation | |
| Lectin binding | FC/FM in combination with lectins | Enables quantification of changes to sperm and sperm surface proteins | |
| Heparin binding | FC/FM with fluorescent heparin (Invitrogen) | Enables quantification of changes in heparin binding to sperm and sperm surface proteins | (Dapino et al., 2006) |
| Anandamide and related compounds interaction with sperm | Capacitation/motility/ viability and acrosome reaction | Agonists and antagonists of Cannabinoid receptors (CB1R and CB2R) modify sperm characteristics in vitro and may be involved in the regulation and activation of capacitation | (Gervasi et al., 2009; Maccarrone, 2009; Maccarrone et al., 2005) |
| Membrane fluidity | FC with merocyanine 540 | Enables quantification of changes in membrane fluidity | (Williamson et al., 1983) |
| Assessment of chromatin integrity | Acridine orange sperm chromatin structure assay (SCSA; uses FC) | Enables quantification of chromatin integrity changes | (Ballachey et al., 1988; Evenson et al., 1980) |
| Sperm migration assay in cervical mucus or the main component of purified hyaluronic acid | Measure sperm migration in glass capillary tube with fluorescent labeled sperm (H33342) | Enables quantification of sperm motility in a media that resembles at least part of the FRT | (Aitken et al., 1992; Gillan et al., 2008) |

TABLE 5-continued

| CHARACTERISTIC | ASSAY | NOTES | REFERENCES |
| --- | --- | --- | --- |
| Neutrophil phagocytosis assay | Microscopic observation of phagocytes and fluorescent labeled sperm (H33342) | Enables quantification of sperm phagocytosis by neutrophils | (Alghamdi et al., 2009; Woelders and Matthijs, 2001) |
| Oviduct explants binding/Annexin-II binding | Binding of fluorescent labeled sperm (H33342) to oviduct. FC in combination with fluorescent labeled Annexin-II protein | Assays enable quantification of ability of sperm to bind to oviduct or the likely receptor on the oviduct | (Ignotz et al., 2007; Teijeiro et al., 2009; Waberski et al., 2005) |
| Lipid peroxidation | FC/FM with C11BODIPY581/591 (Invitrogen) | Enables quantification of membrane lipid peroxidation | (Brouwers and Gadella, 2003) |
| In vitro fertilization | Do with titration of sperm | Enables overall quantification of the ability of sperm to bind zona pellucida, penetrate zona pellucida and fertilize the oocyte | (Amann and Hammerstedt, 2002; Lu and Seidel, 2004; Saeki et al., 1995) | a) Day 1—Bovine Sperm Purification using Percoll™ PLUS

A 90% Percoll™ PLUS solution is made by adding 10× NCM to Percoll™ PLUS. A 60% single layer gradient is then made by dilution with 1× NCM. In the standard method, 4 ml of 60% Percoll™ PLUS/NCM is added in a 15 ml falcon tube, 1.5 ml of ejaculate in liquid extender (standard tris-egg yolk, extension~1:4 egg yolk-citrate-glycerol) is then gently loaded on top, and centrifuged at 700×g for 20 min at room temperature. The pellet is removed and washed once in 8 ml of NCM by centrifugation for 5 min at 700×g. The supernatant is then removed and the pellet resuspended in 1 ml of NCM. Capacitation treatment tubes are set up at a sperm concentration of $5 \times 10^7$ cells/ml.

b) Day 1—Flow Cytometry Analysis

Samples are prepared for flow cytometry analysis as follows. The components shown in Table 6 below are incubated with $5 \times 10^5$ Percoll™ PLUS-purified bovine sperm in a final volume of 200 μl at room temperature for 10 min, while propidium iodide (PI) is added just before analyzing by flow cytometry.

TABLE 6

| FLUORESCENT COMPONENT | FINAL CONCENTRATION | SUPPLIER |
| --- | --- | --- |
| Propidium iodide | 0.3 μM | Invitrogen |
| PNA-alexa fluor 647 | 0.25 μg/mL | Invitrogen |
| SBTI-alexa fluor 488 | 0.01 μg/mL | Invitrogen |
| WGA-fluorescein or WGA-alexa fluor 647 | 0.00625 μg/mL | Invitrogen | c) Day 1—Incubation of Bovine Sperm Sample Overnight

Percoll™ PLUS-purified bovine sperm at $5 \times 10^7$ cells/mL concentration are incubated in NCM overnight in a 28° C. water bath. The sperm are then visually assessed under inverted bright field microscope and/or using QualiSperm prior to inducing capacitation.

d) Day 2—Transition of Cells from Non Capacitating Media to Capacitating Media

After overnight incubation, the cells are diluted in to CM (Table 4). Specifically, 1 ml of overnight incubated sperm is diluted 1:1 with 1 ml of CM media. Activators for capacitation, specifically caffeine and db-cAMP are added at a final concentration of 1 mM (~16 hours after incubation started), and IBMX is added at a final concentration of 100 mM. Alternatively, bovine sperm capacitation is induced using heparin or methylbeta cyclodextrin (cholesterol acceptor). Samples are then incubated for an hour at 37° C.

e) Day 2—Flow Cytometry Analysis of Capacitated Sperm

Similar to day 1, bovine sperm samples are then incubated with fluorescently labeled SBTI, PNA and WGA for 10 mins and PI added just prior to flow analysis.

Example 5

In Vitro Sperm Testing

A series of experiments are performed in vitro to determine the ability of sperm pegylation to improve various measures of sperm functionality in the sperm maturation model of Example 4. Sperm are compared with and without pegylation for changes in the following characteristics: motility; membrane integrity; mitochondrial membrane potential; membrane fluidity; chromatin integrity; lipid peroxidation; capacitation; acrosome reaction; binding of antibodies, heparin and lectins to the sperm surface (or modified sperm surface proteins); ability of sperm to migrate in the FRT; the resistance of sperm to phagocytosis; and the ability of sperm to fertilize in vitro (see Table 5 for details).

Example 6

Binding of Cholesterol-PEG-Fluorescein to Sperm

The ability of cholesterol-PEG-fluorescein to bind to bovine sperm and to human Jurkat cells was assessed by flow cytometry as follows.

Percoll™ PLUS purified bovine sperm ($5 \times 10^5$ cells) were diluted in NCM containing 0.1 mg/ml of BSA, and incubated with either 1 or 10 μg/ml of cholesterol-PEG 2000-fluorescein or cholesterol-PEG 5000-fluorescein for 30 min at 37° C. Similarly, human Jurkat cells ($5 \times 10^5$) were diluted in PBS and incubated with either 1 or 10 μg/ml of cholesterol-PEG 2000-fluorescein or cholesterol-PEG 5000-fluorescein for 30 min at 37° C. After incubation, samples were washed with NCM/BSA or PBS, and cells recovered by centrifugation for 7 min at 3900 rpm at room temperature and removal of supernatant. The cell pellet was resuspended in 190 μl of NCM containing 0.1 mg/ml of BSA for bovine sperm and 190 μl of PBS for Jurkat cells. Cells were then analyzed by flow cytometry.

Table 7 shows the results of studies on the binding of cholesterol-PEG-fluorescein to bovine sperm.

TABLE 7

| Compound | Concentration (µg/ml) | Molecular weight | Concentration (µM) | Fold shift (compared to background) as assessed by flow cytometry |
|---|---|---|---|---|
| Background for Fluorescein | | | | 1 |
| DSPE-PEG 2000-Fluorescein | 1 | 3165.81 | 0.32 | 5 |
| | 10 | 3165.81 | 3.16 | 20 |
| Chol-PEG 2000-Fluorescein | 1 | 2718.9 | 0.37 | 10 |
| | 10 | 2718.9 | 3.68 | 200 |
| Chol-PEG 5000-Fluorescein | 1 | 5718.95 | 0.17 | 10 |
| | 10 | 5718.95 | 1.75 | 100 |

Table 8 shows the results of studies on the binding of cholesterol-PEG-fluorescein to human Jurkat cells.

TABLE 8

| Compound | Concentration (µg/ml) | Molecular weight | Concentration (µM) | Fold shift (compared to background) as assessed by flow cytometry |
|---|---|---|---|---|
| Background for Fluorescein | | | | 1 |
| DSPE-PEG 2000-Fluorescein | 1 | 3165.81 | 0.32 | 10 |
| | 10 | 3165.81 | 3.16 | 100 |
| Chol-PEG 2000-Fluorescein | 1 | 2718.9 | 0.37 | 8 |
| | 10 | 2718.9 | 3.68 | 80 |
| Chol-PEG 5000-Fluorescein | 1 | 5718.95 | 0.17 | 100 |
| | 10 | 5718.95 | 1.75 | 1000 |

Example 7

Binding of PEG to Sperm Cells Via a Reactive Amine Group

The ability of N-hydroxylsuccinimide (NHS)-PEG to bind to sperm cells was examined as follows.

200 µl of 5×10$^7$ sperm cells/ml in NCM containing 0.1 mg/ml of BSA was incubated with 100 µg/ml of NHS-10K-PEG or NHS-20K-PEG light protected at 37° C. for 30 min. 1 ml of 60% Percoll™ PLUS in NCM was placed into a 2 mL tube and 200 µl of each sperm-PEG sample was layered on top of the Percoll™ gradient, followed by centrifuging at 700×g for 20 min in a swinging bucket rotor. The sperm pellet was removed and placed in a new tube. NCM-BSA was added to the pellet to bring the total volume up to 400 µl 40 µl of cells were then transferred to a v-bottom 96-well plate and stained with B47 anti-methoxy-PEG rabbit monoclonal antibody (Epitomics), washed, stained with an Alexa 488-anti-rabbit antibody, washed and the cells analyzed by flow cytometry. The results are shown in Table 9 below.

TABLE 9

| Treatment | Antibodies | NHS-PEG Concentration (µg/ml) | Fold shift (compared to background) as assessed by flow cytometry |
|---|---|---|---|
| Sperm alone from bull 1 | B47 + anti-rabbit-488 | 0 | 1 |
| Sperm from bull 1 + mPEG-10,000-NHS | B47 + anti-rabbit-488 | 100 | 25 |
| Sperm from bull 1 + mPEG-20,000-NHS | B47 + anti-rabbit-488 | 100 | 15 |
| Sperm alone from bull 2 | B47 + anti-rabbit-488 | 0 | 1 |
| Sperm from bull 2 + mPEG-10,000-NHS | B47 + anti-rabbit-488 | 100 | 25 |
| Sperm from bull 2 + mPEG-20,000-NHS | B47 + anti-rabbit-488 | 100 | 10 |

Example 8

In Vivo Field Artificial Insemination Trials

Achieving pregnancy is dependent upon both the male and female fertility, and also upon other factors (such as management of animals, parity, age, environment, insemination procedure etc.) and thus usually requires large numbers of animals in trials (Amann and Hammerstedt, 2002). At least for the bovine, the large number of sperm/ejaculate and also careful study design mean that many sources of variation can be controlled. In cattle, AI trials have been conducted to look at number of sperm required for insemination either alone (Den Daas et al., 1998) or in conjunction with other variables such as flow cytometry sorting (Bodmer et al., 2005), extender composition or other modification (Amann et al., 1999). The basic design is a sperm dose response using several bulls and a large number of cows (Den Daas et al., 1998). Alternatively, heterospermic inseminations with mixtures of sperm from different males followed by embryo recovery and genotyping can be employed to quickly determine fertility of modified sperm, be it flow cytometry sorted or surface modified (Dziuk, 1996; Flint et al., 2003).

BIBLIOGRAPHY

Abuchowski, A., McCoy, J. R., Palczuk, N. C., van Es, T., and Davis, F. F. (1977a). Effect of covalent attachment of polyethylene glycol on immunogenicity and circulating life of bovine liver catalase. J Biol Chem 252, 3582-3586.

Abuchowski, A., van Es, T., Palczuk, N. C., and Davis, F. F. (1977b). Alteration of immunological properties of bovine serum albumin by covalent attachment of polyethylene glycol. J Biol Chem 252, 3578-3581.

Aitken, R. J., Bowie, H., Buckingham, D., Harkiss, D., Richardson, D. W., and West, K. M. (1992). Sperm penetration into a hyaluronic acid polymer as a means of monitoring functional competence. J Androl 13, 44-54.

Alghamdi, A. S., Lovaas, B. J., Bird, S. L., Lamb, G. C., Rendahl, A. K., Taube, P. C., and Foster, D. N. (2009). Species-specific interaction of seminal plasma on sperm-neutrophil binding. Anim Reprod Sci 774, 331-344.

Alvarez, J. G., and Storey, B. T. (1985). Spontaneous lipid peroxidation in rabbit and mouse epididymal spermatozoa: dependence of rate on temperature and oxygen concentration. Biol Reprod 32, 342-351.

Amann, R. P., and Hammerstedt, R. H. (2002). Detection of differences in fertility. J Androl 23, 317-325.

Amann, R. P., Seidel, G. E., Jr., and Brink, Z. A. (1999). Exposure of thawed frozen bull sperm to a synthetic peptide before artificial insemination increases fertility. J Androl 20, 42-46.

Andrade, E. V., Albuquerque, F. C., Moraes, L. M., Brigido, M. M., and Santos-Silva, M. A. (2000). Single-chain Fv with Fc fragment of the human IgG1 tag: construction, *Pichia pastoris* expression and antigen binding characterization. J Biochem 128, 891-895.

Ashworth, P. J., Harrison, R. A., Miller, N. G., Plummer, J. M., and Watson, P. F. (1995). Flow cytometric detection of bicarbonate-induced changes in lectin binding in boar and ram sperm populations. Mol Reprod Dev 40, 164-176.

Baker, M. A., Hetherington, L., Reeves, G., Muller, J., and Aitken, R. J. (2008a). The rat sperm proteome characterized via IPG strip prefractionation and LC-MS/MS identification. Proteomics 5, 2312-2321.

Baker, M. A., Hetherington, L., Reeves, G. M., and Aitken, R. J. (2008b). The mouse sperm proteome characterized via IPG strip prefractionation and LC-MS/MS identification. Proteomics 8, 1720-1730.

Ballachey, B. E., Evenson, D. P., and Saacke, R. G. (1988). The sperm chromatin structure assay. Relationship with alternate tests of semen quality and heterospermic performance of bulls. J Androl 9, 109-115.

Bodmer, M., Janett, F., Hassig, M., den Daas, N., Reichert, P., and Thun, R. (2005). Fertility in heifers and cows after low dose insemination with sex-sorted and non-sorted sperm under field conditions. Theriogenology 64, 1647-1655.

Brouwers, J. F., and Gadella, B. M. (2003). In situ detection and localization of lipid peroxidation in individual bovine sperm cells. Free Radic Biol Med 35, 1382-1391.

Calvete, J. J., Mann, K., Sanz, L., Raida, M., and Topfer-Petersen, E. (1996). The primary structure of BSP-30K, a major lipid-, gelatin-, and heparin-binding glycoprotein of bovine seminal plasma. FEBS Lett 399, 147-152.

Calvete, J. J., and Sanz, L. (2007). Insights into structure-function correlations of ungulate seminal plasma proteins. Soc Reprod Fertil Suppl 65, 201-215.

Centurion, F., Vazquez, J. M., Calvete, J. J., Roca, J., Sanz, L., Parrilla, I., Garcia, E. M., and Martinez, E. A. (2003). Influence of porcine spermadhesins on the susceptibility of boar spermatozoa to high dilution. Biol Reprod 69, 640-646.

Chandonnet, L., Roberts, K. D., Chapdelaine, A., and Manjunath, P. (1990). Identification of heparin-binding proteins in bovine seminal plasma. Mol Reprod Dev 26, 313-318.

Chen, A. M., and Scott, M. D. (2001). Current and future applications of immunological attenuation via pegylation of cells and tissue. BioDrugs 15, 833-847.

Constantine, K. L., Madrid, M., Banyai, L., Trexler, M., Patthy, L., and Llinas, M. (1992). Refined solution structure and ligand-binding properties of PDC-109 domain b. A collagen-binding type II domain. J Mol Biol 223, 281-298.

Cross, N. L., and Watson, S. K. (1994). Assessing acrosomal status of bovine sperm using fluoresceinated lectins, Theriogenology 42, 89-98.

Dapino, D. G., Marini, P. E., and Cabada, M. O. (2006). Effect of heparin on in vitro capacitation of boar sperm. Biol Res 39, 631-639.

Davis, G. T., Bedzyk, W. D., Voss, E. W., and Jacobs, T. W. (1991). Single chain antibody (SC-A) encoding genes: one-step construction and expression in eukaryotic cells. Biotechnology (N Y) 9, 165-169.

de Lamirande, E., and Gagnon, C. (1995). Impact of reactive oxygen species on spermatozoa: a balancing act between beneficial and detrimental effects. Hum Reprod 10 Suppl 1, 15-21.

Den Daas, J. H., De Jong, G., Lansbergen, L. M., and Van Wagtendonk-De Leeuw, A. M. (1998). The relationship between the number of spermatozoa inseminated and the reproductive efficiency of individual dairy bulls. J Dairy Sci 81, 1714-1723.

Desnoyers, L., and Manjunath, P. (1992). Major proteins of bovine seminal plasma exhibit novel interactions with phospholipid. J Biol Chem 267, 10149-10155.

Dostalova, Z., Calvete, J. J., Sanz, L., Hettel, C., Riedel, D., Schoneck, C., Einspanier, R., and Topfer-Petersen, E. (1994). Immunolocalization and quantitation of acidic seminal fluid protein (aSFP) in ejaculated, swim-up, and capacitated bull spermatozoa. Biol Chem Hoppe Seyler 375, 457-461.

Dostalova, Z., Calvete, J. J., Sanz, L., and Topfer-Petersen, E. (1995). Boar spermadhesin AWN-1. Oligosaccharide and zona pellucida binding characteristics. Eur J Biochem 230, 329-336.

Drobnis, E. Z., and Overstreet, J. W. (1992). Natural history of mammalian spermatozoa in the female reproductive tract. Oxf Rev Reprod Biol 14, 1-45.

Durand, H., and Clanet, M. (1988). Genetic improvement of *Trichoderma reesei* for large scale cellulase production. Enzyme Microb Technol 10, 341-346.

Dziuk, P. J. (1996). Factors that influence the proportion of offspring sired by a male following heterospermic insemination. Animal Reproduction Science 43, 65-88.

Ehrlich, P. H., Matsueda, G. R., Margolies, M. N., Husain, S. S., and Haber, E. (1980). Isolation of an active heavy-chain variable domain from a homogeneous rabbit antibody by cathepsin B digestion of the aminoethylated heavy chain. Biochemistry 19, 4091-4096.

Einspanier, R., Einspanier, A., Wempe, F., and Scheit, K. H. (1991). Characterization of a new bioactive protein from bovine seminal fluid. Biochem Biophys Res Commun 179, 1006-1010.

Ekhlasi-Hundrieser, M., Gohr, K., Wagner, A., Tsolova, M., Petrunkina, A., and Topfer-Petersen, E. (2005). Spermadhesin AQN1 is a candidate receptor molecule involved in the formation of the oviductal sperm reservoir in the pig. Biol Reprod 73, 536-545.

Eldin, P., Pauza, M. E., Hieda, Y., Lin, G., Murtaugh, M. P., Pentel, P. R., and Pennell, C. A. (1997). High-level secretion of two antibody single chain Fv fragments by *Pichia pastoris*. J Immunol Methods 201, 67-75.

Evenson, D. P., Darzynkiewicz, Z., and Melamed, M. R. (1980). Relation of mammalian sperm chromatin heterogeneity to fertility. Science 210, 1131-1133.

Flint, A. F., Chapman, P. L., and Seidel, G. E., Jr. (2003). Fertility assessment through heterospermic insemination of flow-sorted sperm in cattle. J Anim Sci 81, 1814-1822.

Focarelli, R., Francavilla, S., Francavilla, F., Delia Giovampaola, C, Santucci, A., and Rosati, F. (1999). A sialoglycoprotein, gp20, of the human capacitated sperm surface is a homologue of the leukocyte CD52 antigen: analysis of the effect of anti-CD52 monoclonal antibody (CAMPATH-1) on capacitated spermatozoa. Mol Hum Reprod 5, 46-51.

Focarelli, R., Giuffrida, A., Capparelli, S., Scibona, M., Menchini Fabris, F., Francavilla, F., Francavilla, S., Giovampaola, CD., and Rosati, F. (1998). Specific localization in the equatorial region of gp20, a 20 kDa sialylglycoprotein of the capacitated human spermatozoon acquired during epididymal transit which is necessary to penetrate zona-free hamster eggs. Mol Hum Reprod 4, 119-125.

Focarelli, R., Giuffrida, A., and Rosati, F. (1995). Changes in the sialylglycoconjugate distribution on the human sperm surface during in-vitro capacitation: partial purification of a 20 kDa sialylglycoprotein of capacitated spermatozoa. Hum Reprod 10, 2755-2759.

Freyre, F. M., Vazquez, J. E., Ayala, M., Canaan-Haden, L., Bell, H., Rodriguez, I., Gonzalez, A., Cintado, A., and Gavilondo, J. V. (2000). Very high expression of an anti-carcinoembryonic antigen single chain Fv antibody fragment in the yeast *Pichia pastoris*. J Biotechnol 76, 157-163.

Frijters, A. C., Mullaart, E., Roelofs, R. M., van Hoorne, R. P., Moreno, J. F., Moreno, O., and Merton, J. S. (2009). What affects fertility of sexed bull semen more, low sperm dosage or the sorting process? Theriogenology 71, 64-67.

Gadella, B. M., and Harrison, R. A. (2002). Capacitation induces cyclic adenosine 3',5'-monophosphate-dependent, but apoptosis-unrelated, exposure of aminophospholipids at the apical head plasma membrane of boar sperm cells. Biol Reprod 67, 340-350.

Garcia, E. M., Vazquez, J. M., Calvete, J. J., Sanz, L., Caballero, I., Parrilla, I., Gil, M. A., Roca, J., and Martinez, E. A. (2006). Dissecting the protective effect of the seminal plasma spermadhesin PSP-I/PSP-II on boar sperm functionality. J Androl 27, 434-443.

Gervasi, M. G., Rapanelli, M., Ribeiro, M. L., Farina, M., Billi, S., Franchi, A. M., and Perez Martinez, S. (2009). The endocannabinoid system in bull sperm and bovine oviductal epithelium: role of anandamide in sperm-oviduct interaction. Reproduction 137, 403-414.

Gillan, L., Evans, G., and Maxwell, W. M. (2005). Flow cytometric evaluation of sperm parameters in relation to fertility potential. Theriogenology 63, 445-457.

Gillan, L., Kroetsch, T., Maxwell, W. M., and Evans, G. (2008). Assessment of in vitro sperm characteristics in relation to fertility in dairy bulls. Anim Reprod Sci 103, 201-214.

Gouka, R. J., Punt, P. J., and van den Hondel, C. A. (1997). Efficient production of secreted proteins by *Aspergillus*: progress, limitations and prospects. Appl Microbiol Biotechnol 47, 1-11.

Greenwald, R. B., Choe, Y. H., McGuire, J., and Conover, C. D. (2003). Effective drug delivery by PEGylated drug conjugates. Adv Drug Deliv Rev 55, 217-250.

Gwathmey, T. M., Ignotz, G. G., Mueller, J. L., Manjunath, P., and Suarez, S. S. (2006). Bovine seminal plasma proteins PDC-109, BSP-A3, and BSP-30-kDa share functional roles in storing sperm in the oviduct. Biol Reprod 75, 501-507.

Harlow, E., and Lane, D. (1988). Antibodies: A laboratory Manual (Cold Spring Harbor Laboratory).

Harper, C. V., Cummerson, J. A., White, M. R., Publicover, S. J., and Johnson, P. M. (2008). Dynamic resolution of acrosomal exocytosis in human sperm. J Cell Sci 121, 2130-2135.

Harris, J. M., and Chess, R. B. (2003). Effect of pegylation on pharmaceuticals. Nat Rev Drug Discov 2, 214-221.

Hawk, H. W. (1983). Sperm survival and transport in the female reproductive tract. J Dairy Sci 66, 2645-2660.

Hochman, J., Gavish, M., Inbar, D., and Givol, D. (1976). Folding and interaction of subunits at the antibody combining site. Biochemistry 15, 2706-2710.

Horwitz, A. H., Chang, C P., Better, M., Hellstrom, K. E., and Robinson, R. R. (1988). Secretion of functional antibody and Fab fragment from yeast cells. Proc Natl Acad Sci USA 85, 8678-8682.

Howes, E. A., Hurst, S., Laslop, A., and Jones, R. (1998). Cellular distribution and molecular heterogeneity of MAC393 antigen (clusterin, beta-chain) on the surface membrane of bull spermatozoa. Mol Hum Reprod 4, 673-681.

Hunter, R. H. (2003). Advances in deep uterine insemination: a fruitful way forward to exploit new sperm technologies in cattle. Anim Reprod Sci 79, 157-170.

Ignotz, G. G., Cho, M. Y., and Suarez, S. S. (2007). Annexins are candidate oviductal receptors for bovine sperm surface proteins and thus may serve to hold bovine sperm in the oviductal reservoir. Biol Reprod 77, 906-913.

Inbar, D., Hochman, J., and Givol, D. (1972). Localization of antibody-combining sites within the variable portions of heavy and light chains. Proc Natl Acad Sci U S A 69, 2659-2662.

Jackson, C. J., Charlton, J. L., Kuzminski, K., Lang, G. M., and Sehon, A. H. (1987). Synthesis, isolation, and characterization of conjugates of ovalbumin with monomethoxypolyethylene glycol using cyanuric chloride as the coupling agent. Anal Biochem 165, 114-127.

Jimenez, I., Gonzalez-Marquez, H., Ortiz, R., Herrera, J. A., Garcii, A., Betancourt, M., and Fierro, R. (2003). Changes in the distribution of lectin receptors during capacitation and acrosome reaction in boar spermatozoa. Theriogenology 59, 1171-1180.

Johnson, L. A., Flook, J. P., and Hawk, H. W. (1989). Sex preselection in rabbits: live births from X and Y sperm separated by DNA and cell sorting. Biol Reprod 41, 199-203.

Jones, R., Mann, T., and Sherins, R. (1979). Peroxidative breakdown of phospholipids in human spermatozoa, spermicidal properties of fatty acid peroxides, and protective action of seminal plasma. Fertil Steril 31, 531-537.

Katz, D. F., Drobnis, E. Z., and Overstreet, J. W. (1989). Factors regulating mammalian sperm migration through the female reproductive tract and oocyte vestments. Gamete Res 22, 443-469.

Keranen, S., and Penttila, M. (1995). Production of recombinant proteins in the filamentous fungus *Trichoderma reesei*. Curr Opin Biotechnol 6, 534-537.

Killian, G. J., Chapman, D. A., and Rogowski, L. A. (1993). Fertility-associated proteins in Holstein bull seminal plasma. Biol Reprod 49, 1202-1207.

Knappik, A., Ge, L., Honegger, A., Pack, P., Fischer, M., Wellnhofer, G., Hoess, A., Wolle, J., Pluckthun, A., and Virnekas, B. (2000). Fully synthetic human combinatorial antibody libraries (HuCAL) based on modular consensus frameworks and CDRs randomized with trinucleotides. J Mol Biol 296, 57-86.

Kodera, Y., Matsushima, A., Hiroto, M., Nishimura, H., Ishii, A., Ueno, T., and Inada, T. (1998). Pegylation of proteins and bioactive substances for medical and technical applications. Progress in Polymer Science 23, 1233-1271.

Kohler, G., and Milstein, C. (1976). Derivation of specific antibody-producing tissue culture and tumor lines by cell fusion. Eur J Immunol 6, 511-519.

Koppers, A. J., De Iuliis, G. N., Finnie, J. M., McLaughlin, E. A., and Aitken, R. J. (2008). Significance of mitochondrial reactive oxygen species in the generation of oxidative stress in spermatozoa. J Clin Endocrinol Metab 93, 3199-3207.

Krebs, B., Rauchenberger, R., Reiffert, S., Rothe, C, Tesar, M., Thomassen, E., Cao, M., Dreier, T., Fischer, D., Hoss, A., et al. (2001). High-throughput generation and engineering of recombinant human antibodies. J Immunol Methods 254, 67-84.

Lane, M., Therien, I., Moreau, R., and Manjunath, P. (1999). Heparin and high-density lipoprotein mediate bovine sperm capacitation by different mechanisms. Biol Reprod 60, 169-175.

Lefebvre, J., Fan, J., Chevalier, S., Sullivan, R., Carmona, E., and Manjunath, P. (2007). Genomic structure and tissue-specific expression of human and mouse genes encoding homologues of the major bovine seminal plasma proteins. Mol Hum Reprod 13, 45-53.

Lightfoot, R. J., and Restall, B. J. (1971). Effects of site of insemination, sperm motility and genital tract contractions on transport of spermatozoa in the ewe. J Reprod Fertil 26, 1-13.

Lu, K. H., and Seidel, G. E., Jr. (2004). Effects of heparin and sperm concentration on cleavage and blastocyst development rates of bovine oocytes inseminated with flow cytometrically-sorted sperm. Theriogenology 62, 819-830.

Maccarrone, M. (2009). Endocannabinoids: friends and foes of reproduction. Prog Lipid Res 48,344-354.

Maccarrone, M., Barboni, B., Paradisi, A., Bernabo, N., Gasperi, V., Pistilli, M. G., Fezza, F., Lucidi, P., and Mattioli, M. (2005). Characterization of the endocannabinoid system in boar spermatozoa and implications for sperm capacitation and acrosome reaction. J Cell Sci 118, 4393-4404.

Mahmoud, A. I., and Parrish, J. J. (1996). Oviduct fluid and heparin induce similar surface changes in bovine sperm during capacitation: a flow cytometric study using lectins. Mol Reprod Dev 43, 554-560.

Manjunath, P., Bergeron, A., Lefebvre, J., and Fan, J. (2007). Seminal plasma proteins: functions and interaction with protective agents during semen preservation. Soc Reprod Fertil Suppl 65, 217-228.

Manjunath, P., and Sairam, M. R. (1987). Purification and biochemical characterization of three major acidic proteins (BSP-A1, BSP-A2 and BSP-A3) from bovine seminal plasma. Biochem J 241, 685-692.

Manjunath, P., and Therien, I. (2002). Role of seminal plasma phospholipid-binding proteins in sperm membrane lipid modification that occurs during capacitation. J Reprod Immunol 53, 109-119.

Matthijs, A., Engel, B., and Woelders, H. (2003). Neutrophil recruitment and phagocytosis of boar spermatozoa after artificial insemination of sows, and the effects of inseminate volume, sperm dose and specific additives in the extender. Reproduction 125, 357-367.

Maxwell, W. M., de Graaf, S. P., Ghaoui Rel, H., and Evans, G. (2007). Seminal plasma effects on sperm handling and female fertility. Soc Reprod Fertil Suppl 64, 13-38.

Medeiros, C. M., and Parrish, J. J. (1996). Changes in lectin binding to bovine sperm during heparin-induced capacitation. Mol Reprod Dev 44, 525-532.

Mitchell, J. R., Senger, P. L., and Rosenberger, J. L. (1985). Distribution and retention of spermatozoa with acrosomal and nuclear abnormalities in the cow genital tract. J Anim Sci 61, 956-967.

Moura, A. A., Koc, H., Chapman, D. A., and Killian, G. J. (2006). Identification of proteins in the accessory sex gland fluid associated with fertility indexes of dairy bulls: a proteomic approach. J Androl 27, 201-211.

Mullins, K. J., and Saacke, R. G. (1989). Study of the functional anatomy of bovine cervical mucosa with special reference to mucus secretion and sperm transport. Anat Rec 225, 106-117.

Nagy, S., Jansen, J., Topper, E. K., and Gadella, B. M. (2003). A triple-stain flow cytometric method to assess plasma- and acrosome-membrane integrity of cryopreserved bovine sperm immediately after thawing in presence of egg-yolk particles. Biol Reprod 68, 1828-1835.

Nauc, V., and Manjunath, P. (2000). Radioimmunoassays for bull seminal plasma proteins (BSP-A1/-A2, BSP-A3, and BSP-30-Kilodaltons), and their quantification in seminal plasma and sperm. Biol Reprod 63, 1058-1066.

Nevalainen, H., Suominen, P., and Taimisto, K. (1994). On the safety of *Trichoderma reesei*. J Biotechnol 37, 193-200.

Nyyssonen, E., Penttila, M., Harkki, A., Saloheimo, A., Knowles, J. K., and Keranen, S. (1993). Efficient production of antibody fragments by the filamentous fungus *Trichoderma reesei*. Biotechnology (N Y) 11, 591-595.

Oren-Benaroya, R., Kipnis, J., and Eisenbach, M. (2007). Phagocytosis of human post-capacitated spermatozoa by macrophages. Hum Reprod 22, 2947-2955.

Pennell, C. A., and Eldin, P. (1998). In vitro production of recombinant antibody fragments in *Pichia pastoris*. Res Immunol 149, 599-603.

Punt, P. J., van Biezen, N., Conesa, A., Albers, A., Mangnus, J., and van den Hondel, C. (2002). Filamentous fungi as cell factories for heterologous protein production. Trends Biotechnol 20, 200-206.

Radzio, R., and Kuck, U. (1997). Synthesis of biotechnologically relevant heterologous proteins in filamentous fungi. Process Biochem 32, 529-539.

Rathi, R., Colenbrander, B., Bevers, M. M., and Gadella, B. M. (2001). Evaluation of in vitro capacitation of stallion spermatozoa. Biol Reprod 65, 462-470.

Rauchenberger, R., Borges, E., Thomassen-Wolf, E., Rom, E., Adar, R., Yaniv, Y., Malka, M., Chumakov, I., Kotzer, S., Resnitzky, D., et al. (2003). Human combinatorial Fab library yielding specific and functional antibodies against the human fibroblast growth factor receptor 3. J Biol Chem 278, 38194-38205.

Ridder, R., Schmitz, R., Legay, F., and Gram, H. (1995). Generation of rabbit monoclonal antibody fragments from a combinatorial phage display library and their production in the yeast *Pichia pastoris*. Biotechnology (N Y) 13, 255-260.

Roberts, M. J., Bentley, M. D., and Harris, J. M. (2002). Chemistry for peptide and protein PEGylation. Adv Drug Deliv Rev 54, 459-476.

Saeki, K., Nagao, Y., Hoshi, M., and Nagai, M. (1995). Effects of heparin, sperm concentration and bull variation on in vitro fertilization of bovine oocytes in a protein-free medium. Theriogenology 43, 751-759.

Salicioni, A. M., Platt, M. D., Wertheimer, E. V., Arcelay, E., Allaire, A., Sosnik, J., and Visconti, P. E. (2007). Signalling pathways involved in sperm capacitation. Soc Reprod Fertil Suppl 65, 245-259.

Schroter, S., Osterhoff, C, McArdle, W., and Ivell, R. (1999). The glycocalyx of the sperm surface. Hum Reprod Update 5, 302-313.

Scott, M. D., Murad, K. L., Koumpouras, F., Talbot, M., and Eaton, J. W. (1997). Chemical camouflage of antigenic determinants: stealth erythrocytes. Proc Natl Acad Sci USA 94, 7566-7571.

Senior, J., Delgado, C, Fisher, D., Tilcock, C, and Gregoriadis, G. (1991). Influence of surface hydrophilicity of liposomes on their interaction with plasma protein and clearance from the circulation: studies with poly(ethylene glycol)-coated vesicles. Biochim Biophys Acta 1062, 77-82.

Shapiro, H. M., Natale, P. J., and Kamentsky, L. A. (1979). Estimation of membrane potentials of individual lymphocytes by flow cytometry. Proc Natl Acad Sci U S A 76, 5728-5730.

Sharpe, J. C., and Evans, K. M. (2009). Advances in flow cytometry for sperm sexing. Theriogenology 71, 4-10.

Stein, K. K., Go, J. C., Lane, W. S., Primakoff, P., and Myles, D. G. (2006). Proteomic analysis of sperm regions that mediate sperm-egg interactions. Proteomics 6, 3533-3543.

Storey, B. T. (1997). Biochemistry of the induction and prevention of lipoperoxidative damage in human spermatozoa. Mol Hum Reprod 3, 203-213.

Storey, B. T. (2008). Mammalian sperm metabolism: oxygen and sugar, friend and foe. Int J Dev Biol 52, 427-437.

Swennen, D., Paul, M. F., Vernis, L., Beckerich, J. M., Fournier, A., and Gaillardin, C. (2002). Secretion of active anti-Ras single-chain Fv antibody by the yeasts *Yarrowia lipolytica* and *Kluyveromyces lactis*. Microbiology 148, 41-50.

Taitzoglou, I. A., Kokoli, A. N., and Killian, G. J. (2007). Modifications of surface carbohydrates on bovine spermatozoa mediated by oviductal fluid: a flow cytometric study using lectins. Int J Androl 30, 108-114.

Tedeschi, G., Oungre, E., Mortarino, M., Negri, A., Maffeo, G., and Ronchi, S. (2000). Purification and primary structure of a new bovine spermadhesin. Eur J Biochem 267, 6175-6179.

Teijeiro, J. M., Ignotz, G. G., and Marini, P. E. (2009). Annexin A2 is involved in pig (Sus scrofa)sperm-oviduct interaction. Mol Reprod Dev 76, 334-341.

Tejerina, F., Buranaamnuay, K., Saravia, F., Wallgren, M., and Rodriguez-Martinez, H. (2008). Assessment of motility of ejaculated, liquid-stored boar spermatozoa using computerized instruments. Theriogenology 69, 1129-1138.

Teramura, Y., and Iwata, H. (2009). Surface modification of islets with PEG-lipid for improvement of graft survival in intraportal transplantation. Transplantation 88, 624-630.

Therien, I., Bergeron, A., Bousquet, D., and Manjunath, P. (2005). Isolation and characterization of glycosaminoglycans from bovine follicular fluid and their effect on sperm capacitation. Mol Reprod Dev 71, 97-106.

Therien, I., Bleau, G., and Manjunath, P. (1995). Phosphatidylcholine-binding proteins of bovine seminal plasma modulate capacitation of spermatozoa by heparin. Biol Reprod 52, 1372-1379.

Therien, I., Bousquet, D., and Manjunath, P. (2001). Effect of seminal phospholipid-binding proteins and follicular fluid on bovine sperm capacitation. Biol Reprod 65, 41-51.

Therien, I., Moreau, R., and Manjunath, P. (1998). Major proteins of bovine seminal plasma and high-density lipoprotein induce cholesterol efflux from epididymal sperm. Biol Reprod 59, 768-776.

Therien, I., Soubeyrand, S., and Manjunath, P. (1997). Major proteins of bovine seminal plasma modulate sperm capacitation by high-density lipoprotein. Biol Reprod 57, 1080-1088.

Tollner, T. L., Vandevoort, C. A., Yudin, A. I., Treece, C. A., Overstreet, J. W., and Cherr, G. N. (2009). Release of DEFB126 from macaque sperm and completion of capacitation are triggered by conditions that simulate periovulatory oviductal fluid. Mol Reprod Dev 76, 431-443.

Tollner, T. L., Yudin, A. I., Tarantal, A. F., Treece, C. A., Overstreet, J. W., and Cherr, G. N. (2008a). Beta-defensin 126 on the surface of macaque sperm mediates attachment of sperm to oviductal epithelia. Biol Reprod 78, 400-412.

Tollner, T. L., Yudin, A. I., Treece, C. A., Overstreet, J. W., and Cherr, G. N. (2008b). Macaque sperm coating protein DEFB126 facilitates sperm penetration of cervical mucus. Hum Reprod 23, 2523-2534.

Topfer-Petersen, E., Ekhlasi-Hundrieser, M., Tsolova, M., Leeb, T., Kirchhoff, C, and Muller, P. (2005). Structure and function of secretory proteins of the male genital tract. Andrologia 37, 202-204.

Topfer-Petersen, E., Romero, A., Varela, P. F., Ekhlasi-Hundrieser, M., Dostalova, Z., Sanz, L., and Calvete, J. J. (1998). Spermadhesins: a new protein family. Facts, hypotheses and perspectives. Andrologia 30, 217-224.

Vazquez, J. M., Martinez, E. A., Roca, J., Gil, M. A., Parrilla, I., Cuello, C, Carvajal, G., Lucas, X., and Vazquez, J. L. (2005). Improving the efficiency of sperm technologies in pigs: the value of deep intrauterine insemination. Theriogenology 63, 536-547.

Vazquez, J. M., Roca, J., Gil, M. A., Cuello, C, Parrilla, I., Vazquez, J. L., and Martinez, E. A. (2008). New developments in low-dose insemination technology. Theriogenology 70, 1216-1224.

Verdoes, J. C., Punt, P. J., and van den Hondel, C. (1995). Molecular genetic strain improvement for the overproduction of fungal proteins by Filamentous fungi. Appl Microbiol Biotechnol 43, 195-205.

Vernet, P., Fulton, N., Wallace, C, and Aitken, R. J. (2001). Analysis of reactive oxygen species generating systems in rat epididymal spermatozoa. Biol Reprod 65, 1102-1113.

Waberski, D., Magnus, F., Mendonca Ferreira, F., Petrunkina, A. M., Weitze, K. F., and Topfer-Petersen, E. (2005). Importance of sperm-binding assays for fertility prognosis of porcine spermatozoa. Theriogenology 63, 470-484.

Wah, D. A., Fernandez-Tornero, C, Sanz, L., Romero, A., and Calvete, J. J. (2002). Sperm coating mechanism from the 1.8 A crystal structure of PDC-109-phosphorylcholine complex. Structure 10, 505-514.

Wang, Z., Widgren, E. E., Richardson, R. T., and O'Rand, M. G. (2007). Characterization of an eppin protein complex from human semen and spermatozoa. Biol Reprod 77, 476-484.

Ward, M., Wilson, L. J., Kodama, K. H., Rey, M. W., and Berka, R. M. (1990). Improved production of chymosin in *Aspergillus* by expression as a glucoamylase-chymosin fusion. Biotechnology (N Y) 8, 435-440.

Wempe, F., Einspanier, R., and Scheit, K. H. (1992). Characterization by cDNA cloning of the mRNA of a new growth factor from bovine seminal plasma: acidic seminal fluid protein. Biochem Biophys Res Commun 183, 232-237.

Williamson, P., Mattocks, K., and Schlegel, R. A. (1983). Merocyanine 540, a fluorescent probe sensitive to lipid packing. Biochim Biophys Acta 732, 387-393.

Woelders, H., and Matthijs, A. (2001). Phagocytosis of boar spermatozoa in vitro and in vivo. Reprod Suppl 58, 113-127.

Yamaguchi, R., Muro, Y., Isotani, A., Tokuhiro, K., Takumi, K., Adham, I., Ikawa, M., and Okabe, M. (2009). Disruption of ADAM3 impairs the migration of sperm into oviduct in mouse. Biol Reprod 81, 142-146.

Yudin, A., Tollner, T., Treece, C, Kays, R., Cherr, G., Overstreet, J., and Bevins, C. (2008). {beta}-defensin 22 is a major component of the mouse sperm glyocalyx. Reproduction 136, 753-765.

Yudin, A. I., Generao, S. E., Tollner, T. L., Treece, C. A., Overstreet, J. W., and Cherr, G. N. (2005). Beta-defensin 126 on the cell surface protects sperm from immunorecognition and binding of anti-sperm antibodies. Biol Reprod 73, 1243-1252.

Zalipsky, S., Brandeis, E., Newman, M. S., and Woodle, M. C. (1994). Long circulating, cationic liposomes containing amino-PEG-phosphatidylethanolamine. FEBS Lett 353, 71-74.

We claim:

1. A method for improving functionality and/or fertility of sperm, comprising contacting the sperm with an effective amount of a composition comprising a component selected from the group consisting of: pegylated membrane anchoring agents: and pegylated seminal plasma proteins.

2. The method of claim 1, wherein the seminal plasma protein is selected from the group consisting of: PDC-109, BSP-A3, BSP-30 kDa, aSFP and Z13.

3. The method of claim 1, wherein the membrane anchoring agent is a lipid.

4. The method of claim 3, wherein the lipid is selected from the group consisting of: cholesterol, diacylglycerolipids, dialkylglycerolipids, glycerophospholipids, sphingosine derived diacyl- and dialkyl lipids, ceramide, phosphatidate, phosphatidyl choline, phosphatidyl ethanolamine, phosphatidyl serine, phosphatidyl inositol and phosphatidyl glycerol.

5. A method for preparing a composition for use in artificial insemination or in vitro fertilization, comprising:
(a) providing sperm from it mammal; and
(b) contacting the sperm with an effective amount of a composition comprising a component selected from the group consisting of: pegylated membrane anchoring agents: and pegylated seminal plasma proteins.

6. The method of claim 5, further comprising sorting the sperm to separate X chromosome bearing sperm trot Y chromosome bearing sperm.

7. The method of claim 5, wherein the mammal is human, bovine, porcine or equine.

8. The method of claim 5, wherein the seminal plasma protein is selected from the group consisting of: PDC-109, BSP-A3, BSP-30 kDa, aSFP and Z13.

9. The method of claim 5, wherein the membrane anchoring agent is a lipid.

10. The method of claim 9, wherein the lipid is selected from the group consisting of: cholesterol, diacylglycerolipids, dialkylglycerolipids, glycerophospholipids, sphingosine derived diacyl- and dialkyl lipids, ceramide, phosphatidate, phosphatidyl choline, phosphatidyl ethanolamine, phosphatidyl serine, phosphatidyl inositol and phosphatidyl glycerol.

11. A preparation comprising live sperm and a pegylated membrane anchoring agent.

12. A preparation comprising live sperm and a pegylated seminal plasma protein.

13. The preparation of claim 12, wherein the seminal plasma protein is selected from the group consisting of: PDC-109, BSP-A3, BSP-30kDa, aSFP and Z13.

14. The preparation of claim 11, wherein the membrane anchoring agent is a lipid.

15. The preparation of claim 14, wherein the lipid is selected from the group consisting of: cholesterol, diacylglycerolipids, dialkylglycerolipids, glycerophospholipids, sphingosine derived diacyl- and dialkyl lipids, ceramide, phosphatidate, phosphatidyl choline, phosphatidyl ethanolamine, phosphatidyl serine, phosphatidyl inositol and phosphatidyl glycerol.

16. The preparation of claim 11, wherein the sperm are X chromosome bearing sperm.

17. The preparation of claim 12, wherein the sperm are X chromosome bearing sperm.

* * * * *

UNITED STATES PATENT AND TRADEMARK OFFICE
CERTIFICATE OF CORRECTION

PATENT NO. : 8,592,138 B2  
APPLICATION NO. : 13/578576  
DATED : November 26, 2013  
INVENTOR(S) : Keith Hudson et al.

Page 1 of 1

It is certified that error appears in the above-identified patent and that said Letters Patent is hereby corrected as shown below:

In the Claims:

| Col. No. | Line(s) | |
|---|---|---|
| 35 | 35 | Replace "sperm from it mammal" with ---sperm from a mammal--- |

Signed and Sealed this
Eleventh Day of February, 2014

Michelle K. Lee
*Deputy Director of the United States Patent and Trademark Office*